(12) United States Patent  (10) Patent No.: US 7,654,992 B2
Yamaki et al.  (45) Date of Patent: Feb. 2, 2010

(54) INTERLABIAL PAD

(75) Inventors: Koichi Yamaki, Kagawa-ken (JP); Megumi Tokumoto, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 11/540,006

(22) Filed: Sep. 29, 2006

(65) Prior Publication Data

US 2007/0078423 A1  Apr. 5, 2007

(30) Foreign Application Priority Data

Oct. 4, 2005   (JP)  ............... 2005-291768

(51) Int. Cl.
*A61F 13/15*  (2006.01)
*A61F 13/20*  (2006.01)

(52) U.S. Cl. .................. 604/385.17; 604/380

(58) Field of Classification Search ............ 604/385.17, 604/385.18, 904, 385.01, 385.101, 367, 379–382
See application file for complete search history.

(56) References Cited

U.S. PATENT DOCUMENTS

2005/0215969 A1*  9/2005  Mizutani et al.  ........ 604/385.17

FOREIGN PATENT DOCUMENTS

| JP | 2004-097693 A | 4/2004 |
|---|---|---|
| JP | 2004-261231 A | 9/2004 |
| JP | 2004-526502 A | 9/2004 |
| JP | 2005-503193 A | 2/2005 |
| WO | WO 02/076362 A | 10/2002 |
| WO | WO 02/094147 A | 11/2002 |
| WO | WO 02/094152 A | 11/2002 |
| WO | WO 02/094153 A | 11/2002 |
| WO | WO 02/094161 A | 11/2002 |
| WO | WO 02/094162 A | 11/2002 |
| WO | WO 02/100315 A | 12/2002 |

* cited by examiner

*Primary Examiner*—Michele Kidwell
(74) *Attorney, Agent, or Firm*—Butzel Long

(57) ABSTRACT

An interlabial pad is provided which is capable of being precisely inserted into the recess between the wearer's labia minora, which does not have a linear shape. An interlabial pad 1 includes a highly-compressed rigid region 10, which is highly resistant to being compressed, at a central region along the center line X-X' in the longitudinal direction. When the interlabial pad is worn, the highly-compressed rigid region 10 protrudes, thereby allowing the wearer to fit the protruding highly-compressed rigid region 10 in the recess between the labia.

12 Claims, 29 Drawing Sheets

INTERLABIAL PAD

This application is based on and claims the benefit of priority from Japanese Patent Application No. 2005-291768, filed on Oct. 4, 2005, the content of which is incorporated herein by reference.

BACKGROUND OF THE INVENTION

1. Field of the Invention

The present invention relates to an interlabial pad having a function of conforming to the shape of the relevant part of the wearer's body when it is being worn, thereby allowing the wearer to properly wear the interlabial pad.

2. Related Art

Examples of conventional feminine hygiene products generally used include sanitary napkins and tampons. Here, a great deal of effort is being put into the development of sanitary napkins which have a function of preventing menstrual blood from leaking from the gap between the sanitary napkin and the wearer's skin, which occurs due to poor adherence of the sanitary napkin to the wearer's skin around the opening of the vagina. On the other hand, the tampons lead to the wearer experiencing feelings of discomfort or foreign-body sensation, and difficulty in inserting the tampon into the vagina. Accordingly, a great deal of effort is also being put into the development of tampons having a function of eliminating such problems.

In such a situation, a sanitary item intermediate between the sanitary napkin and the tampon, the so-called interlabial pad is coming to attract a great deal of attention. The interlabial pad is a sanitary item that has a function of allowing the wearer to wear it by putting a part of the pad between the labia such that it is in contact with the inner face of the labia. As compared with the sanitary napkins, the interlabial pad provides improved adherence of the pad to the wearer's body, thereby preventing menstrual blood from leaking out. Thus, the interlabial pad protects against menstrual blood spreading over a large area of the wearer's body, thereby offering a clean sanitary item. Furthermore, the interlabial pad is smaller than the sanitary napkin, thereby providing greater comfort when it is being worn. On the other hand, as compared with the tampon, which is inserted into the wearer's vagina when it is being worn, the interlabial pad has the advantage of reducing the wearer's psychological resistance to wearing the interlabial pad.

However, the interlabial pad has the following disadvantage. That is to say, the contractile force between the woman's labia allows the interlabial pad to be worn and maintains the adherence of the pad to the wearer's body. Let us consider a case in which the wearer has inserted the interlabial pad improperly. In some cases, such a case causes the interlabial pad to be displaced from the wearer's labia. Also, in some cases, the interlabial pad in this state cannot exhibit satisfactory absorption capacity, leading to the leakage of menstrual blood. Accordingly, there is a demand for an interlabial pad having a function of allowing the wearer to properly wear it in a simple manner, and various interlabial pads having such a function have been studied.

As an example of such an interlabial pad having a function of allowing the wearer to wear it in a simple manner, the PCT Japanese Translation Patent Publication No. 2004-526502 (hereinafter Patent Document 1) discloses an interlabial pad including a tab connected to and hanging from a backing sheet. The tab included in the interlabial pad is relatively stiff. This allows the wearer to easily hold the tab without the tab becoming deformed when the wearer is inserting the interlabial pad between the labia. Furthermore, the tab is not formed so as to be uniformly stiff over the overall length. In other words, there is a difference in the stiffness between the upper portion and the lower portion of the tab. This suppresses the wearer's feelings of discomfort due to the stiffness when the interlabial pad is being worn.

Also, as an another example, PCT Japanese Translation Patent Publication No. 2005-503193 (hereinafter the Patent Document 2) discloses an interlabial pad formed of a liquid-permeable cover, an absorber, and a liquid-impermeable buffer, with joining member such as a strip, slit, adhesive, pleat line, protrusion, or the like, being formed along the center line of the liquid-permeable buffer. The interlabial pad having such a structure allows the wearer to put it on and take it off by inserting the wearer's finger into the joining member or guiding the joining member by the wearer's finger.

DISCLOSURE OF INVENTION

Problems to be Solved by the Invention

While such a structure having the tab and the joining member is helpful for the wearer to easily wear the interlabial pad, such a structure alone is insufficient to provide a function of allowing the wearer to properly wear the interlabial pad. Furthermore, the interlabial pad having such a structure has no function of allowing the wearer to confirm whether or not the wearer is properly wearing it, leading to the wearer remaining concerned about this matter.

The present invention has been made in view of the aforementioned problems. Accordingly, it is an object thereof to provide an interlabial pad having a function of allowing the wearer to easily and properly wear it in an assured manner.

SUMMARY OF THE INVENTION

In order to solve the aforementioned problems, the present inventors provide an interlabial pad having a structure in which a predetermined portion is more resistant to being compressed than are its surroundings so as to conform to the shape of the wearer's body when worn. Specifically, with regard to the interlabial pad, the region corresponding to the recess of the wearer's body when it is being worn is formed such that it is more resistant to being compressed than are the other regions. With such an arrangement, the interlabial pad provides a protrusion which allows the wearer to insert it into the recess of the wearer's body in a manner like that of the wearer fitting a puzzle piece into an appropriate space. More specifically, the present invention provides the following arrangements.

In a first aspect of the interlabial pad of the present invention, the interlabial pad includes: an oblong and liquid-permeable top sheet having a center line as a folding axis; an oblong and liquid-impermeable backing sheet of which the perimeter is connected to the perimeter of the top sheet; an absorber provided between the top sheet and the backing sheet; and a highly-compressed rigid region which is provided on the center line in the absorber, and which has higher resistance to being compressed than that of other regions in the absorber, thereby providing a protrusion corresponding to the thickness of the highly-compressed rigid region when the interlabial pad is being worn after being worn after being folded into two with the center line as a folding axis.

With regard to the interlabial pad according to the first aspect of the present invention, a highly-compressed rigid portion is provided in the region which is to face the vestibule or the opening of the vagina, i.e., the recess of the wearer's body when the interlabial pad is being worn. Such an arrangement enables the interlabial pad to conform to the shape of the portion of the wearer's body into which the interlabial pad is to be inserted. That is to say, the portion of the wearer's body into which the interlabial pad is to be inserted does not have a linear shape, but has a recess around the vestibule or the opening of the vagina with respect to a straight line that connects the clitoris and the posterior commissure of the labia. However, conventional interlabial pads have a flat structure which allows the pad to be in contact with a flat face uniformly. Accordingly, with such a conventional arrangement, upon the interlabial pad being inserted into the recess between the labia, the interlabial pad is folded along any axial line. In this case, the folding axis along which the interlabial pad is folded is a straight line. Furthermore, the thickness and the stiffness are uniform over the longitudinal direction. Such an arrangement provides a uniform and linear portion, leading to difficulty in inserting the interlabial pad into the recess of the wearer's body. In addition, the wearer needs to insert the interlabial pad into the recess between the labia by feel of the finger alone without visual confirmation while holding the interlabial pad by the finger. However, with such an arrangement, if the pad deviates from the proper location, there is a difficulty in detecting the deviation of the interlabial pad by feel of the finger or the labia alone when it is inserted. This leads to a situation in which the wearer inserts the interlabial pad in a wrong manner. In some cases, such a situation results in the leakage of menstrual blood and the displacement of the interlabial pad. Furthermore, the wearer cannot confirm whether or not the interlabial pad has been inserted in a proper manner until the wearer replaces the interlabial pad. Accordingly, the wearer remains concerned about this matter even if the interlabial pad is being worn in a proper manner.

On the other hand, the interlabial pad according to the present invention has a highly-compressed rigid region that maintains its thickness and size at approximately the same level as that before it is worn, and other regions that conform to the shape of the wearer's body. With such an arrangement, only the highly-compressed rigid region protrudes, thereby allowing the wearer to fit the protrusion thus formed into the recess of the wearer's body in a manner like that of the wearer fitting a puzzle piece into an appropriate space when it is being worn. This allows the wearer to wear the interlabial pad in a proper and simple manner. Furthermore, such an arrangement allows the wearer to feel the interlabial pad fit into the recess of the wearer's body, thereby eliminating the concern about whether or not the interlabial pad is being worn in a proper manner.

Note that the aforementioned Patent Document 2 describes that the interlabial pad is preferably formed with a relatively low density so as to give the wearer a feeling of comfort when it is worn. On the other hand, the interlabial pad according to the present invention includes a highly-compressed rigid region having high density. However, such a highly-compressed rigid region fits into the recess of the wearer's body. Such an arrangement improves ease of wearing without reducing comfort.

The term "center line" as used in the present specification represents a line which passes through the center of the pad and extends in the longitudinal direction, along which the interlabial pad is to be folded into two. In FIG. 1, the center line is indicated by "X-X'". On the other hand, the term "central region" as used here represents a region including at least the intersection of the aforementioned center line and the center line along the lateral direction of the interlabial pad. In FIG. 1, the center line along the lateral direction is indicated by "A-A'", and the intersection is indicated by "P". The aforementioned central region is a region which extends with a predetermined width along the lateral direction with the center line X-X' as the center, and which extends with a predetermined length along the longitudinal direction with the intersection P as the center. Specifically, the central region has a size which fits into a space defined by the portion of the wearer's body around the vestibule between the labia minora when the interlabial pad according to the present invention is being worn.

The term "highly-compressed" as used in the present specification means that the subject portion is more resistant to being compressed than are its surroundings. That is to say, upon the application of the same pressure to the subject portion and the surrounding portions that form the product, the subject portion relatively becomes thicker than the surrounding portion. On the other hand, the term "high density" as used here means that the subject portion has a higher density than its surroundings.

In a second aspect of the interlabial pad as described in the first aspect of the present invention, the highly-compressed rigid region is provided at a central region on the center line.

The interlabial pad according to the present invention has the aforementioned highly-compressed rigid region around the central region of the pad. Such an arrangement allows the wearer to insert the portion of the interlabial pad, which has high body-liquid absorption capacity, into the recess between the labia minora, which includes the opening of the vagina, etc., in an assured manner.

In a third aspect of the interlabial pad as described in the first or second aspects of the present invention, the highly-compressed rigid region is provided on the center line with a size of 5 mm to 45 mm along the longitudinal direction.

The interlabial pad according to the third aspect of the present invention has the highly-compressed rigid region with a predetermined size. Here, the average length from the clitoris, around the front opening of the labia minora, to the frenulum of the labia minora, around the rear opening of the labia minora, is 56.5 mm. Giving consideration to this fact, let us consider a case in which the highly-compressed rigid region has a length less than 5 mm, which is very much smaller than the length of the labia minora. In this case, such an arrangement allows the wearer to put the highly-compressed rigid region between the labia minora. However, there are excessively large spaces between one end of the highly-compressed rigid region and the front opening of the labia minora, and between the other one end of the highly-compressed rigid region and the rear opening of the labia minora. Accordingly, in some cases, the interlabial pad deviates from the proper location. On the other hand, let us consider a case in which the highly-compressed rigid region has a length greater than 45 mm. In some cases, this leads to a situation in which the highly-compressed rigid region cannot be fit into the vestibule, and a part of the highly-compressed rigid region protrudes from the labia minora. In some cases, this causes irritation to the clitoris and the frenulum of the labia, leading to the wearer experiencing feelings of discomfort. The present invention provides an interlabial pad having a highly-compressed rigid portion with a size determined giving consideration to the aforementioned problem. Thus, the present invention provides an interlabial pad that allows the wearer to wear it in comfort.

In a fourth aspect of the interlabial pad as described in any one of the first through the third aspects of the present invention, the highly-compressed rigid region has a thickness in the perpendicular direction when the interlabial pad is being worn, which allows the highly-compressed rigid region to fit within a region near the vestibule between the wearer's labia minora.

The interlabial pad according to the fourth aspect of the present invention includes the highly-compressed rigid region having a thickness which allows it to fit into a space near the vestibule between the labia minora. The labia consist of the labia majora and the labia minora. The labia majora are at a position outside of the labia minora around the vestibule between the labia minora. Accordingly, the labia minora can be widely opened around the ends. On the other hand, the labia minora cannot be easily opened around the vestibule due to the inward pressure applied from the left and right labia majora, positioned outside of the labia minora. Accordingly, the labia minora exhibit higher labial pressure around the vestibule than around the ends. Furthermore, there is less change in the labial pressure around the vestibule corresponding to changes in the position of the wearer's body. Note that, in general, such a tendency is satisfied regardless of the shape of the wearer's body. Accordingly, the highly-compressed region is held by such high labial pressure as long as the highly-compressed region is formed with a size that allows it to fit into a space around the vestibule.

Specifically, the highly-compressed rigid region more preferably has a size of 1 to 8 mm. The reason is as follows. The labia minora is an organ that connects the clitoris and the frenulum of the labia. Also, the base of the labia minora is at a position on a shortest distance in space between the clitoris and the frenulum of the labia. The base of the labia minora is supported by the vestibular sphincter, which generates a large contractile force (which allows the highly-compressed rigid region to be held). On the other hand, the portion near the vestibule, at a deeper position than the base of the labia minora, exhibits a smaller contractile force than that around the base of the labia minora, and is less sensitive. On the other hand, the present invention provides the highly-compressed rigid region having the aforementioned size. This allows the highly-compressed rigid region to be fit in a space between the portion near the vestibule and the base of the labia minora. Accordingly, the highly-compressed rigid region is supported by the contractile force generated by the vestibular sphincter. This allows the entire region of the interlabial pad to be held by the contractile force generated by the portion around the vestibule of the labia minora in an assured manner. Furthermore, with such an arrangement, the highly-compressed rigid region is positioned at a less sensitive portion of the wearer's body, thereby allowing the wearer to wear the interlabial pad more comfortably than would be possible if it were positioned at other positions. Furthermore, the wearer adjusts the position of the interlabial pad such that it is worn in comfort. Accordingly, such an arrangement allows the wearer to insert the interlabial pad into the proper position along the perpendicular direction.

In a fifth aspect of the interlabial pad as described in any one of the first through the fourth aspects of the present invention, further includes a transition region around the highly-compressed rigid region, at least in the central region, which provides a change in stiffness in a stepped manner.

The interlabial pad according to the fifth aspect of the present invention further includes a transition region which provides a change in stiffness between the highly-compressed rigid region and its surroundings in a stepped manner. With such an arrangement, the shape of the interlabial pad can be more easily adjusted to the curved shape of the labia minora. This allows the wearer to wear the interlabial pad more comfortably.

In a sixth aspect of the interlabial pad as described in any one of the first through the fifth aspects of the present invention, further includes a finger-insertion pocket which is provided to the face opposite to the wearer's body when the interlabial pad is worn, and which allows the wearer to insert the wearer's finger into the pocket, thereby enabling the highly-compressed rigid region to be positioned at a proper location.

The interlabial pad according to the sixth aspect of the present invention further includes a finger-insertion pocket, which allows the wearer to insert the wearer's finger into the pocket. Such an arrangement allows the wearer to position the wearer's sensitive finger cushion at the position of the highly-compressed rigid region. This helps the wearer to introduce the highly-compressed rigid region to a proper position by the finger, thereby allowing the wearer to wear the interlabial pad more easily in a sure manner.

In a seventh aspect of the interlabial pad as described in the first aspect of the present invention, the highly-compressed rigid region is provided in approximately the shape of the letter "H".

In an eighth aspect of the interlabial pad as described in the first aspect of the present invention, the highly-compressed rigid regions are provided to the central region and to regions along the perimeter extending along the longitudinal direction of the interlabial pad.

In a ninth aspect of the interlabial pad as described in the first aspect of the present invention, the highly-compressed rigid region includes fiber assembly, and in which the fiber assembly provided in the central region is formed with a higher density than that of the other regions.

In a tenth aspect of the interlabial pad as described in the first aspect of the present invention, the highly-compressed rigid region is an embossed region.

In an eleventh aspect of the interlabial pad as described in the eighth aspect of the present invention, the highly-compressed rigid region is an embossed region, with the embossed region being provided to both sides of the center line, parallel to, and in a left-right symmetrical manner with respect to, the center line.

Advantages

The interlabial pad according to the present invention allows the wearer to fit the highly-compressed rigid region into the recess between the clitoris and the opening of the vagina, into which the interlabial pad is to be inserted, in a manner like that of the wearer fitting a puzzle piece into an appropriate space. This allows the wearer to wear the interlabial pad while confirming whether or not the interlabial pad is at a proper position. Furthermore, the interlabial pad properly fits into the recess, thereby preventing bodily liquid from leaking, and suppressing the displacement of the interlabial pad.

DETAILED DESCRIPTION OF THE INVENTION

Figure 1:
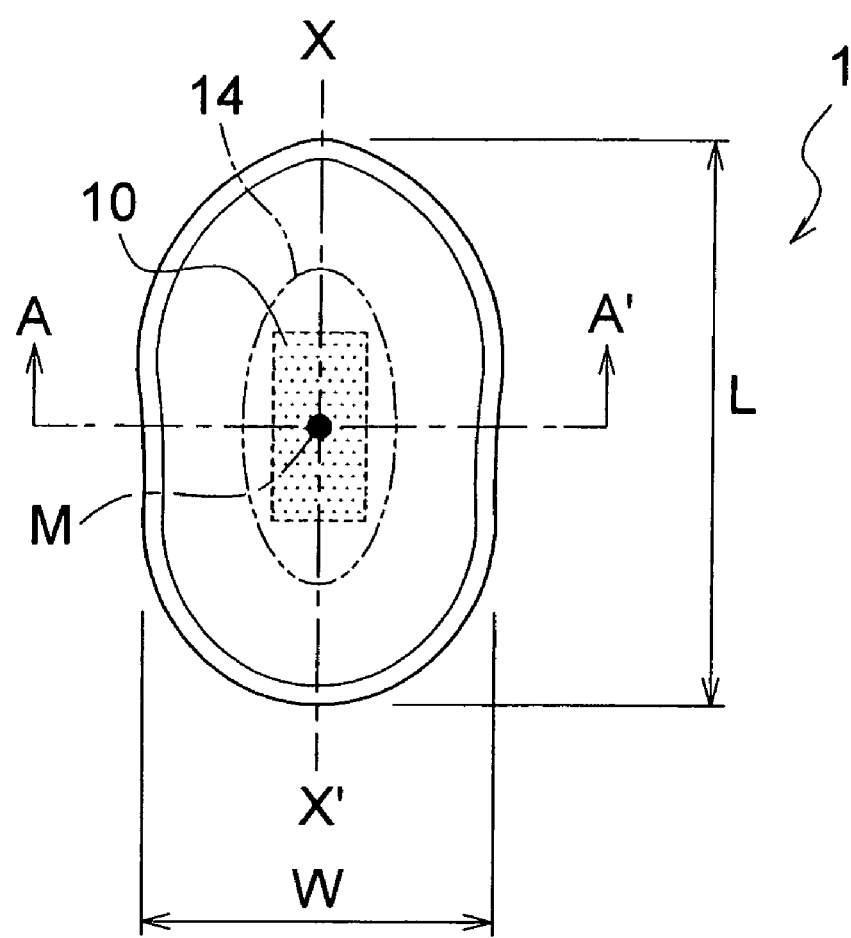
FIG. 1 is a diagram which shows an interlabial pad according to a first embodiment as viewed from the face which is to be in contact with the wearer's body.

Description will be made below regarding embodiments according the present invention with reference to the drawings. Note that in the embodiments other than the first embodiment, the same components as those in the first embodiment are denoted by the same reference numerals, and description thereof will be omitted or simplified.

First Embodiment

Overall Structure of Interlabial Pad

Figure 2:
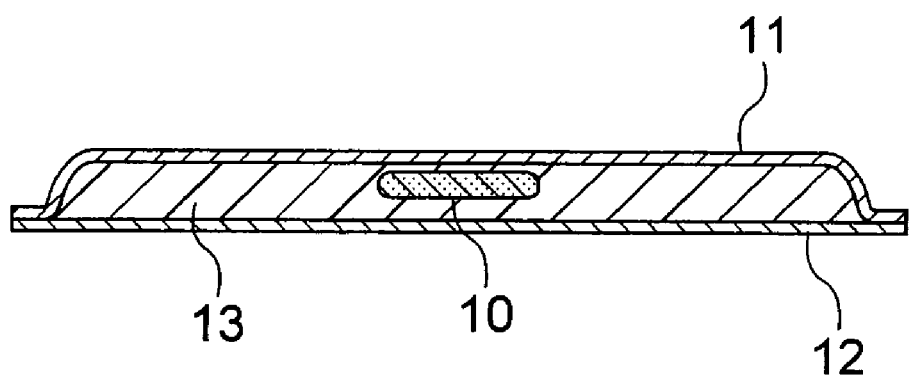
FIG. 2 is a cross-sectional view of the interlabial pad 1 taken along A-A' shown in FIG. 1.

FIG. 1 is a diagram which shows an interlabial pad according to the present embodiment as viewed from the side which is to be in contact with the wearer's body. FIG. 2 is a cross-sectional view taken along line A-A' in FIG. 1.

An interlabial pad 1 according to the present embodiment is formed in an oblong shape as shown in FIG. 1. As shown in FIG. 2, the interlabial pad according to the present embodiment is formed of a liquid-permeable front sheet 11, a liquid-impermeable backing sheet 12, and an absorber 13 introduced between the front sheet 11 and the backing sheet 12. The interlabial pad 1 is worn by the wearer, which is arranged at a wearer's crotch in a front to back direction of the wearer's body. The longitudinal direction of the interlabial pad is corresponding to this front to back direction. In the present specification, "front" means a front of the wearer's body, "back" means a back of the wearer's body. In the present specification, the aforementioned front to back direction will be referred to as the "longitudinal direction L". On the other hand, the direction orthogonal to the longitudinal direction L will be referred to as the "lateral direction W". The interlabial pad 1 has an approximately symmetrical shape with respect to the center line X-X' which is the center line along the longitudinal direction. Furthermore, a highly-compressed rigid region 10 is provided around a central region along the center line X-X'.

State of Interlabial Pad when it is Being Worn

Next, a description will be given regarding change in the shape of the interlabial pad 1 along the longitudinal direction when it is worn. FIGS. 3 through 6 are explanatory diagrams for describing the state of the interlabial pad 1 and the wearer's body as viewed from the side, i.e. from the direction of the wearer's profile.

Figure 3:
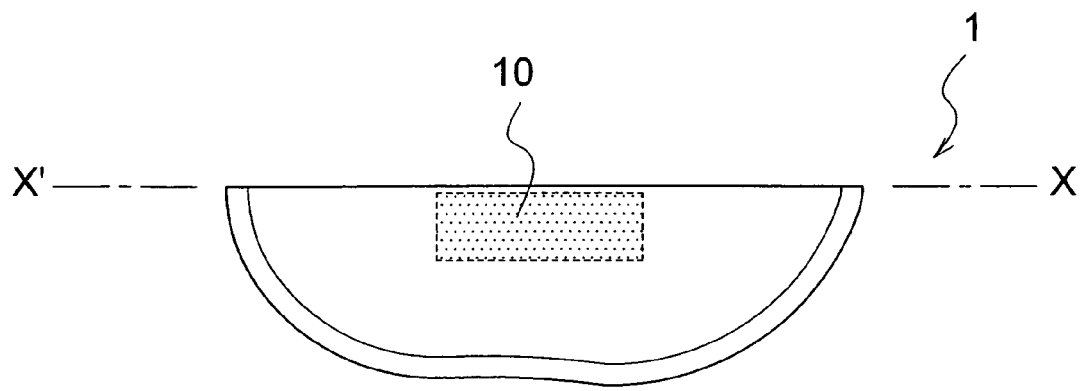
FIG. 3 is a diagram which shows the interlabial pad according to the first embodiment, having been folded into two.
Figure 4:
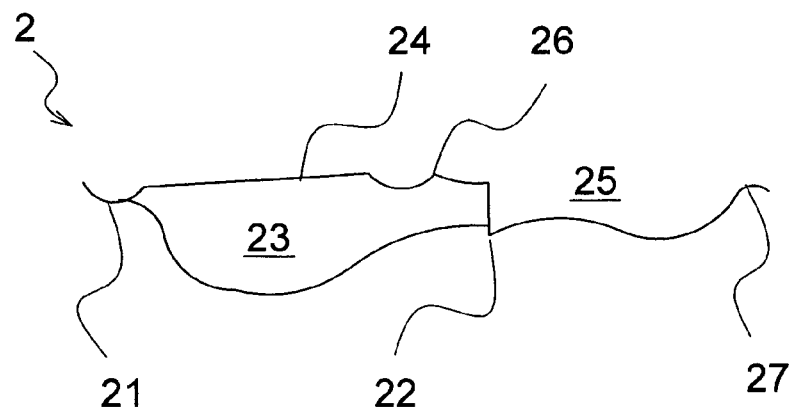
FIG. 4 is a sectional view of the portion of the wearer's body into which the interlabial pad is to be interested.

The interlabial pad 1 is folded into two with the center line X-X' as a folding axis as shown in FIG. 3. On the other hand, the portion of the wearer's body into which the interlabial pad 1 is to be inserted is the inner portion of the labia minora 23 which connects the clitoris 21 and the posterior commissure of the labia 22 (the portion between the labia minora 23 and the other unshown labium minora). A vestibule 24, which is at a position on the inner side of the labia minora, is at a position deeper within the wearer's body than the clitoris 21 and the posterior commissure of the labia 22. Accordingly, the center line of the wearer's body connecting from the clitoris 21 to the perineum 25 is not a straight line, but is a curved line having protrusions and recesses.

Figure 5:
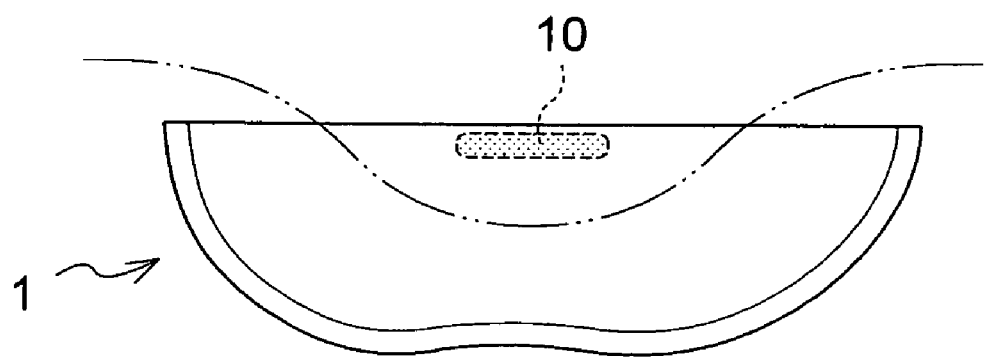
FIG. 5 is a diagram which shows the state of the interlabial pad according to the first embodiment when it is worn.
Figure 6:
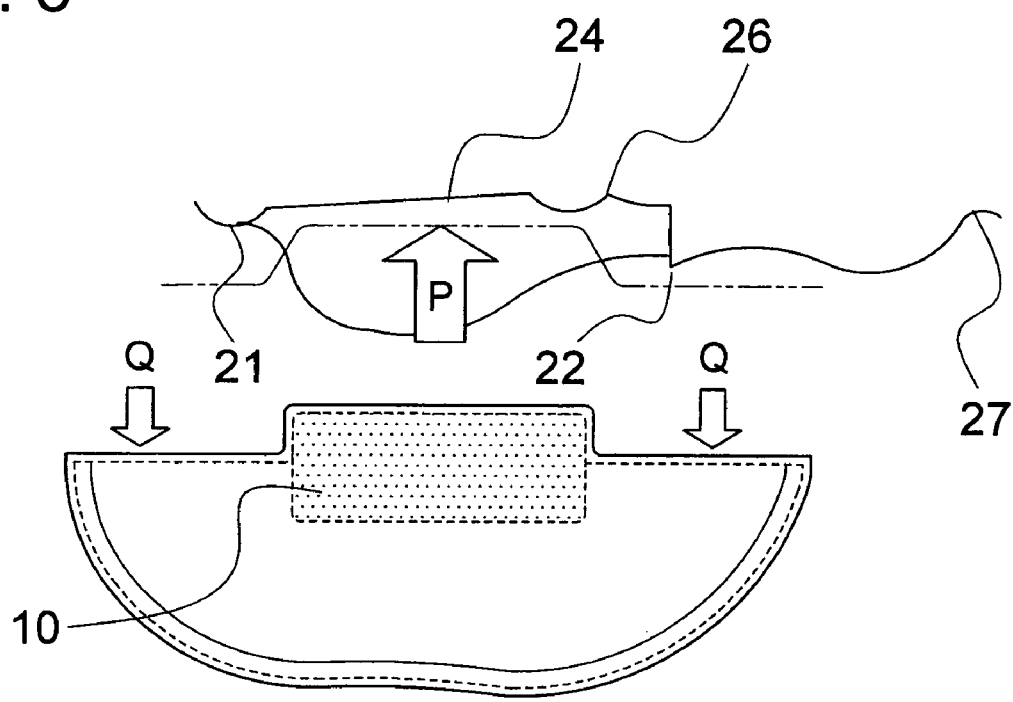
FIG. 6 is a diagram which shows the relation between the interlabial pad according to the first embodiment and the wearer's body when it is being worn.

Giving consideration to such a point, the interlabial pad 1 includes a variable-shape folding axis portion as follows. That is to say, before the interlabial pad 1 is worn, the folding axis portion has a linear shape as shown in FIG. 5. On the other hand, upon the interlabial pad 1 being worn, a part of the folding axis portion protrudes due to the pressure in the direction P applied from the wearer's fingers and the pressure in the direction Q applied from the labia, which are pressed into contact with the interlabial pad 1. (For the sake of convenience of description, the interlabial pad 1 is not in contact with the labia in the drawing. In practice, the surface of the interlabial pad 1 protrudes due to the interlabial pad 1 and the wearer's labia being pressed in contact with one another.) That is to say, when the interlabial pad 1 is inserted, the pressure applied to the folding axis portion reduces the thickness of the folding axis portion other than the highly-compressed rigid region 10 along the height direction. On the other hand, the highly-compressed rigid region, which is resistant to being reduced in thickness, is maintained at approximately the same thickness as that before the interlabial pad is worn. As a result, upon the interlabial pad being worn, the highly-compressed rigid region protrudes. Such an arrangement allows the wearer to fit the highly-compressed rigid region into the recess positioned between the clitoris 21 and the posterior commissure of the labia 22. As described above, such an arrangement allows the wearer to wear the interlabial pad in a manner like that of the wearer fitting a puzzle piece into an appropriate space. This allows the wearer to properly wear the interlabial pad 1 by feel alone without visual confirmation.

Next, a description will be given regarding change in the shape of the interlabial pad along the lateral direction. FIGS. 7 through 10 are diagrams for describing the interlabial pad and the wearer's body as viewed from top (head) or bottom (foot) thereof.

Figure 7:
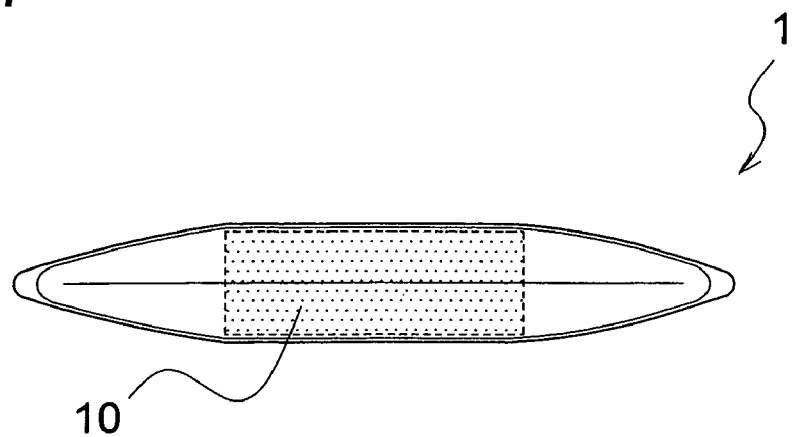
FIG. 7 is a diagram which shows the interlabial pad according to the first embodiment before it is worn and after it is folded into two as viewed from the side which is to be in contact with the wearer's body.
Figure 8:
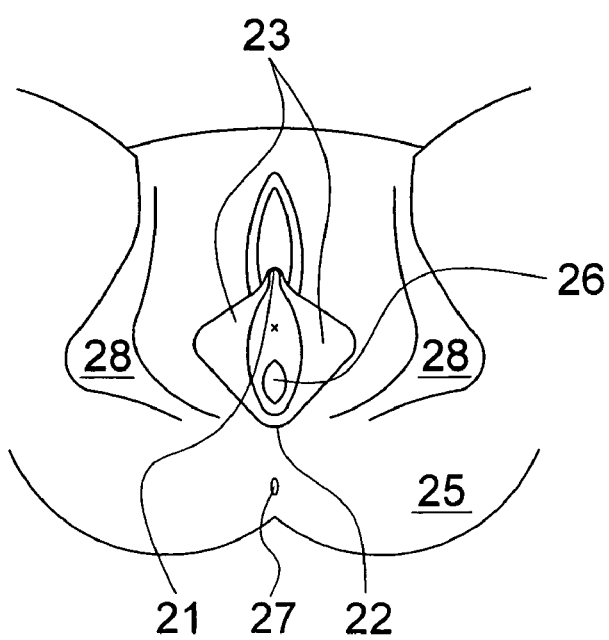
FIG. 8 is a diagram which shows the wearer's body as viewed from below.
Figure 9:
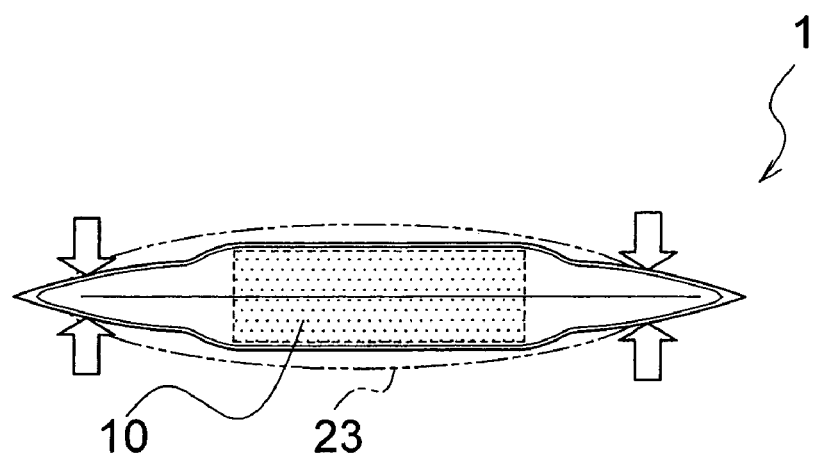
FIG. 9 is a conceptual diagram which shows the highly-compressed region inserted between the labia minora.
Figure 10:
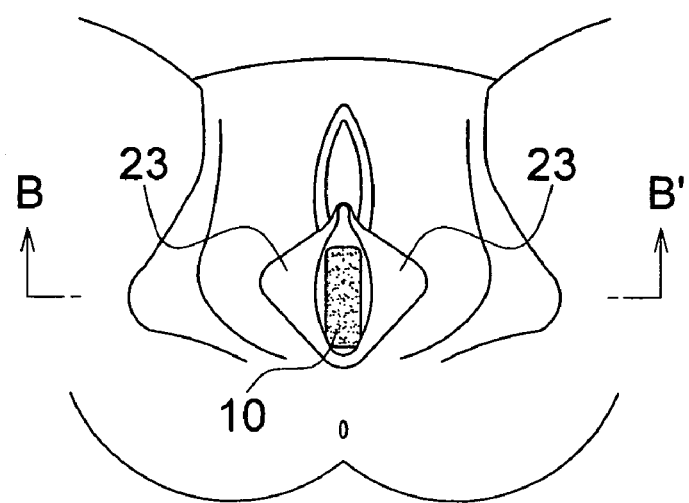
FIG. 10 is an explanatory cutaway diagram which shows the highly-compressed rigid region of the interlabial pad according to the first embodiment, with the other portions omitted.

As shown in FIG. 7, the interlabial pad 1 includes the highly-compressed rigid region 10, which is more resistant to being compressed, around the central region along the longitudinal direction. On the other hand, as shown in FIG. 8, the portion of the wearer's body into which the interlabial pad is to be inserted has a space defined by the left and right labia minora 23, which connect the clitoris 21 and the posterior commissure of the labia 22 (frenulum labiorum pudendi). With regard to this space, the front opening and the rear opening of the labia minora 23 cannot be expanded along the lateral direction. Accordingly, the space into which the interlabial pad is to be put between the labia minora 23 is formed in approximately the shape of a rugby ball. Here, let us consider a situation in which the interlabial pad 1 is inserted into the recess between the labia minora 23. The region other than the highly-compressed rigid region 10 is less resistant to being reduced in thickness along the width direction due to compression by the labia minora 23. Accordingly, such a situation results in reduction of the width of the region other than the highly-compressed rigid region 10. On the other hand, the highly-compressed rigid region 10 is highly resistant to being reduced in thickness along the width direction due to the application of pressure. Accordingly, in such a situation, the highly-compressed rigid region 10 maintains the same width as that before the application of the pressure. Accordingly, after the interlabial pad 1 is fit into the recess between the labia minora 23, as shown in FIG. 9, the interlabial pad 1 changes its shape into that having a larger width around the center than that around the ends. This allows the wearer to easily fit the highly-compressed rigid region 10 into the recess between the left and right labia minora 23, which can be opened in a shape of a rugby ball, in a manner like that of the wearer fitting a puzzle piece into an appropriate space.

Figure 11:
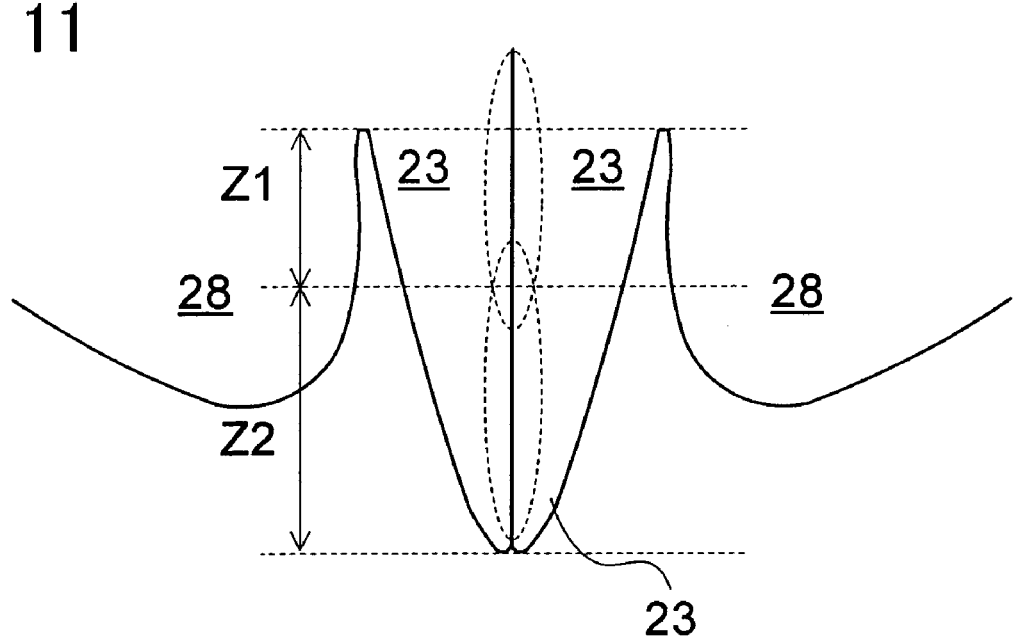
FIG. 11 is a diagram which shows the state of the labia in a case in which the subject stands upright with her legs opened.
Figure 12:
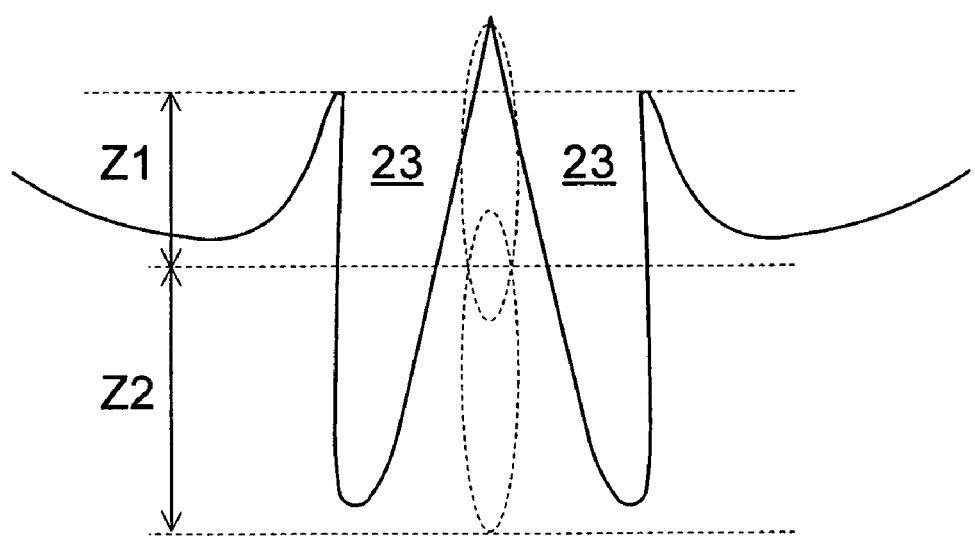
FIG. 12 is a diagram which shows the state of the labia in a case in which the subject stoops down.
Figure 13:
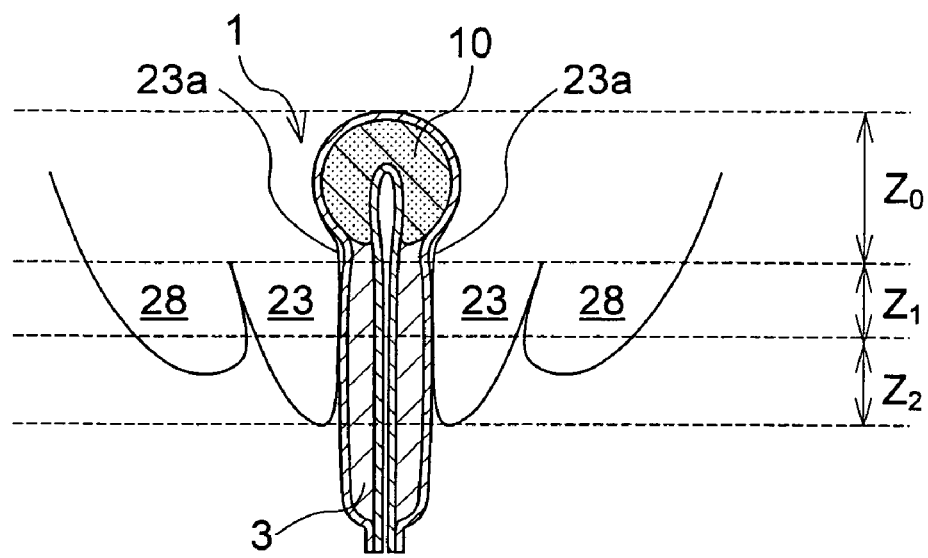
FIG. 13 is a sectional view which shows the interlabial pad inserted between the labia.
Figure 14A:
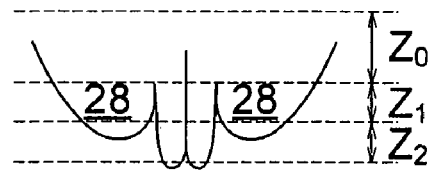
FIGS. 14A to 14C are comparison diagrams for describing the difference in the position into which the interlabial pads are inserted.
Figure 14B:
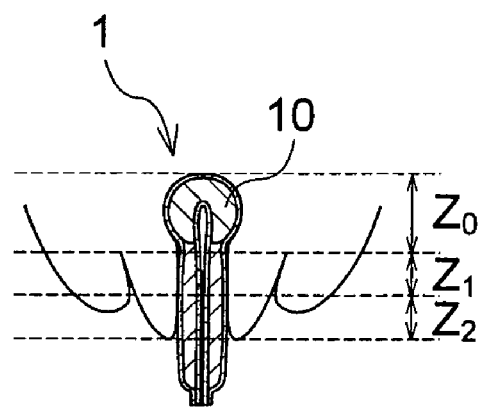
Figure 14C:
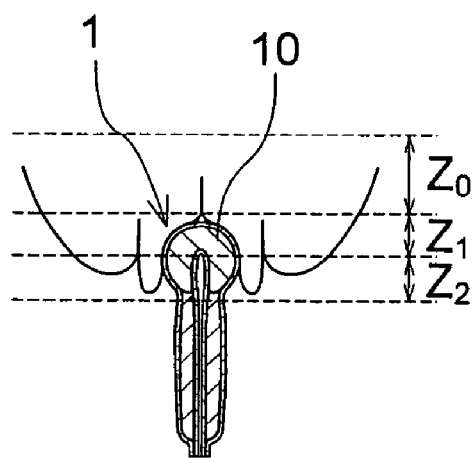

Next, a description will be given regarding the length of the highly-compressed rigid region along the vertical direction when the interlabial pad is worn. FIGS. 11 and 12 are diagrams for describing the states of the wearer's labia, which differs from one another due to the motion of the wearer. FIG. 13 is a cross-sectional view which shows the wearer's labia and the interlabial pad when the interlabial pad is being worn. FIGS. 14A to 14C are diagrams for describing the difference in the position where the interlabial pad is worn.

The highly-compressed rigid region 10 of the interlabial pad 1 is preferably formed with a size which allows it to be fit within a region around the wearer's vestibule between the wearer's labia minora. The reason is that higher pressure (contractile force) is generated between the labia minora around the vestibule than there is around the tips. Note that the pressure between the labia minora can be measured using a contact pressure measurement apparatus (e.g., contact pressure measurement apparatus from NIPPON MMI TECHNOLOGY INC.). With such a contact pressure measurement apparatus, an air pack terminal having a diameter of approximately 12 mm is inserted into the recess between the subject's labia minora, thereby measuring the pressure between the subject's labia minora. For example, let us consider a case in which a subject having a BMI value (=weight [kg]/height [m]/height [m]) of 19.3 stands upright with her legs opened (with an interval of 35 cm between the left and right toes). In this state, the tips of the labia minora 23 are closed as shown in FIG. 11. In this case, the labia minora exhibit labial pressure of 0.49 N/cm$^2$ around the vestibule Z1. The labia minora exhibit labial pressure of 0.42 N/cm$^2$ around the tips Z2 thereof. That is to say, the pressure between the labia around the vestibule is approximately 1.2 times as high as that around the tips Z2 of the labia minora. On the other hand, let us consider a case in which the same subject stoops down (with an interval of 35 cm between the left and right knees, and with an interval of 35 cm between the left and right toes). In this case, the tips of the labia minora 23 are opened as shown FIG. 12. In this state, the labia minora exhibit the labia pressure of 0.12 N/cm$^2$ around the vestibule Z1. The labia minora exhibit the labia pressure of 0 N/cm$^2$ around the tips of the labia minora Z2. Accordingly, in either case, the pressure between the labia around the vestibule is higher than that around the tips of the labia small 23. Accordingly, the highly-compressed rigid region 10 of the interlabial pad 1 is preferably formed with a size which allows it to be fit within a region around the vestibule between the wearer's labia minora, as described above.

More preferably, the highly-compressed rigid region 10 is formed with a size of 1 mm to 8 mm from the side which is to be in contact with the vestibule to the opposite side along the vertical direction in the drawing. Specific description will be made below. Let us say that the interlabial pad includes the highly-compressed rigid region formed of compressed pulp having a density of 400 g/m$^2$. Furthermore, let us consider a case in which such an interlabial pad is worn after it is folded into two with the longitudinal center line as a folding axis such that the backing sheets thereof face one another. In this case, the highly-compressed rigid region 10 is preferably formed from the center line in a direction towards the periphery of the interlabial pad with a length of 1 mm to 8 mm.

With such an arrangement, the interlabial pad 1 has an inverted U-shaped cross-sectional shape with each respective edge being attached when it is being inserted into the recess between the labia minora 23 positioned on the inner sides of the wearer's labia majora pudendi 28, as shown in FIG. 13. In this state, the highly-compressed rigid region 10 has a greater thickness than that of the peripheral region 3. On the other hand, with regard the portion of the wearer's body into which the interlabial pad is to be inserted, the labia minora exhibit greater contractile force around the base of the labia minora 23a than that exhibited around the portion Z1 around the vestibule. Furthermore, the wearer is less sensitive around the portion Z0 near the vestibule. Giving consideration to the structure of the interlabial pad 1 and the nature of each portion of the wearer's body, the highly-compressed rigid region 10 is preferably formed with a size along the vertical direction in the drawing such that it can fit within the region Z0 near the vestibule. From such a perspective, with the present embodiment, the highly-compressed rigid region 10 is formed with such a size described above. Such an arrangement allows the highly-compressed rigid region 10 to fit within the region Z0 near the vestibule. Furthermore, in this state, the other region 3 is held around the vestibule. This prevents the displacement of the interlabial pad 1.

Furthermore, the highly-compressed rigid region 10 having such a size described above also offers the advantage of serving as a guide which helps the wearer to properly wear the interlabial pad. Specifically, in general, the interlabial pad 1 is fitted between the labia minora in a closed state. When the interlabial pad 1 is worn, the state in which the highly-compressed rigid region 10 is positioned at the less sensitive region Z1 near the vestibule as shown in FIG. 14B offers greater comfort than the state in which the highly-compressed rigid region 10 is positioned at the sensitive region Z2 around the tips of the labia minora protruding along the vertical direction as shown in FIG. 14C. Accordingly, the interlabial pad including the highly-compressed rigid region 10 with such a size as described above allows the wearer to adjust the position of the highly-compressed rigid region 10 to be within the region Z0 near the vestibule based upon what the wearer feels as it is being inserted. This allows the wearer to properly wear the interlabial pad 1 with respect to the vertical direction in the drawing. Furthermore, in this state, the highly-compressed rigid region 10 put between the labia minora is positioned at a deeper location around the vestibule than the bases 23a of the labia minora. This means that the highly-compressed rigid region 10 is held by the contractile force (which allows the interlabial pad to be held) from the vestibular sphincter around the bases 23a of the labia minora. This allows the interlabial pad to be held around the vestibule, thereby holding the interlabial pad firmly between the labia.

Material of Highly-Compressed Rigid Region

The highly-compressed rigid region 10 according to the present embodiment exhibits greater resistance to being compressed than that exhibited by the peripheral region. Specifically, let us consider a case of the application of pressure of 2 N/cm$^2$ to the interlabial pad in the form of a manufactured product. In this case, the highly-compressed rigid region 10 maintains its thickness at a level greater than that of the peripheral region, to which the same pressure has been applied, within a range of 0.5 mm to 3 mm. Specifically, the highly-compressed rigid region 10 is formed as follows. That is to say, pulverized pulp having a density of 200 to 600 g/m$^2$ is multi-layered, and is compressed under high pressure by embossing, thereby forming compressed pulp. The compressed pulp thus formed is provided to the absorber which is a component of the interlabial pad 1, thereby forming the highly-compressed rigid region 10. Instead of such a structure in which compressed pulp is provided to the absorber, the material that exhibits the high stiffness and high resistance to being compressed may be formed of layered pulp pressed by embossing or the like, for example. Also, such a material may be formed as follows. First, a single-type fiber, a core/sheath fiber, a deflected-core core/sheath fiber, or a side-by-side type fiber is formed of thermoplastic resin such as polyurethane foam, polyethylene, polypropylene, polyethylene terephthalate, or the like. Then, a single-layer or multi-layered and single-type or composite non-woven fabric is formed of the fiber thus prepared, by the water flow entangling method, the spunbonding method, or the like, thereby obtaining the material of the highly-compressed rigid region 10. A description will be given below regarding a specific example. First, a non-woven fabric having a density of 20 g/m$^2$ is formed of a polyethylene or polypropylene core/sheath fiber with 4.4 dtex and with a fiber length of 51 mm using the through-air method. Furthermore, layered pulp is applied to the non-woven fabric thus formed so as to form a layered structure having a density of 200 g/m². Furthermore, the layered structure thus formed is fixed by thermal embossing so as to have an embossed pattern formed of dot-shaped embossed portions each of which has an area of 1 mm², and which are arrayed at an angle of 30 degrees.

Modification 1

Next, a description will be given regarding a modification of a structure of the highly-compressed rigid region. FIGS. 15 through 19 are diagrams for describing an interlabial pad according to a Modification 1. FIGS. 20 through 24 are diagrams for describing an interlabial pad according to a Modification 2. Each of such modifications shown in these drawings has a structure in which pulp is provided to a predetermined part so as to form the highly-compressed rigid region, and no pulp is provided to the other part, thereby more effectively improving the functions of the highly-compressed rigid region. Also, FIGS. 25 through 30 are diagrams for describing an interlabial pad according to a Modification 3, having a structure in which the highly-compressed rigid region is formed by adjusting the density of the fiber bundles that form the absorber. FIGS. 31 through 34 are diagrams for describing an interlabial pad according to a Modification 4, having a structure which allows the wearer to use it without folding it into two.

Figure 15:
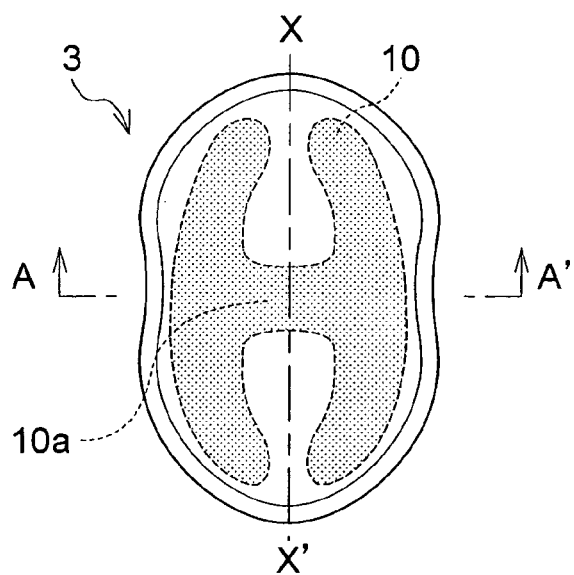
FIG. 15 is a diagram which shows a highly-compressed rigid region of an interlabial pad according to a modification 1 of the first embodiment.
Figure 16:
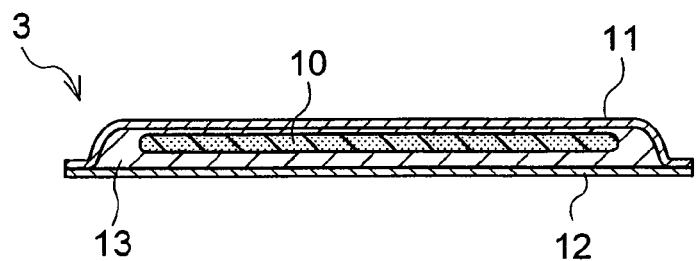
FIG. 16 is a cross-sectional view taken along line A-A' in FIG. 15.

An interlabial pad 3 shown in FIG. 15 has a structure in which the highly-compressed rigid region 10 is provided in approximately the shape of the letter "H". With such a structure, as shown in FIG. 16, the highly-compressed rigid region 10 is provided with a wider area than that shown in FIG. 2. This improves the bodily fluid absorption capacity thereof. Furthermore, with such a structure, no pulp is provided along the center line X-X' extending in the longitudinal direction, except for the central region 10a. Such a structure enables the central region 10a of the highly-compressed rigid region 10 to easily protrude when it is being inserted. Furthermore, such a structure suppresses the wearer's feelings of discomfort around the clitoris and the posterior commissure of the labia due to irritation from the interlabial pad 3. The highly-compressed rigid region 10 has an approximately H-shaped structure having a central region 10a formed with a pulp density of 400 g/m², and other region formed with a pulp density of 200 g/m. Note that the central region 10a formed of pulp may be subjected to embossing.

Figure 17:
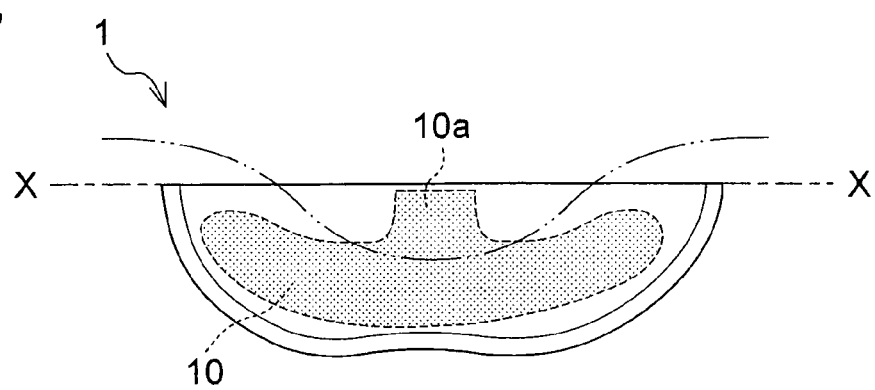
FIG. 17 is a diagram which shows the folded interlabial pad according to the modification 1 as viewed from the side.
Figure 18:
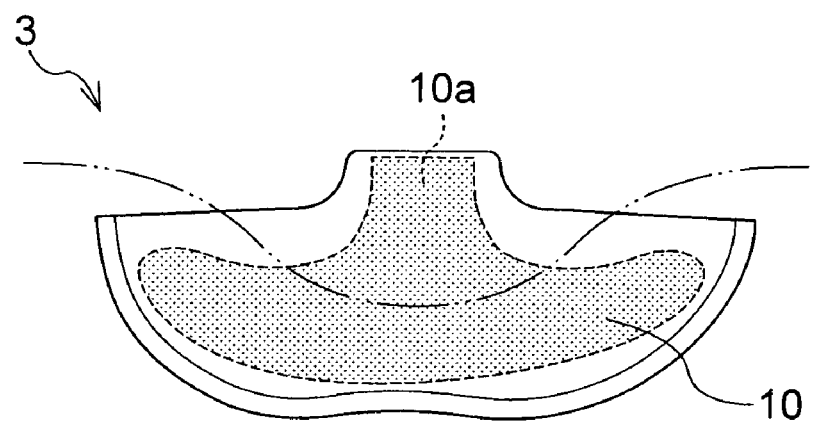
FIG. 18 is a diagram which shows the interlabial pad according to the modification 1 changing in shape when it is being inserted.
Figure 19:
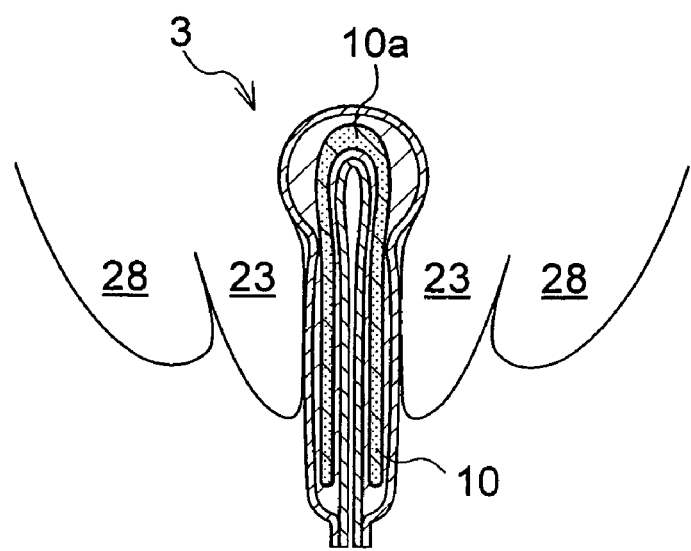
FIG. 19 is a sectional view which shows the interlabial pad according to the modification 1 when it is being worn.

Let us say that the interlabial pad 3 is folded along the longitudinal direction with the center line X-X' as a reference as shown in FIG. 17. In this stage, the central region 10a protruding from the highly-compressed rigid region 10 is stored in the interlabial pad 3, and does not protrude from the surface of the pad. Upon the wearer inserting the interlabial pad 3 in such a state, the central region of the interlabial pad protrudes from the surface of the interlabial pad as shown in FIG. 18. Note that the highly-compressed rigid region 10 around the central portion along the vertical direction in FIG. 19 is formed with a wide area extending along the longitudinal direction.

Modification 2

Figure 20:
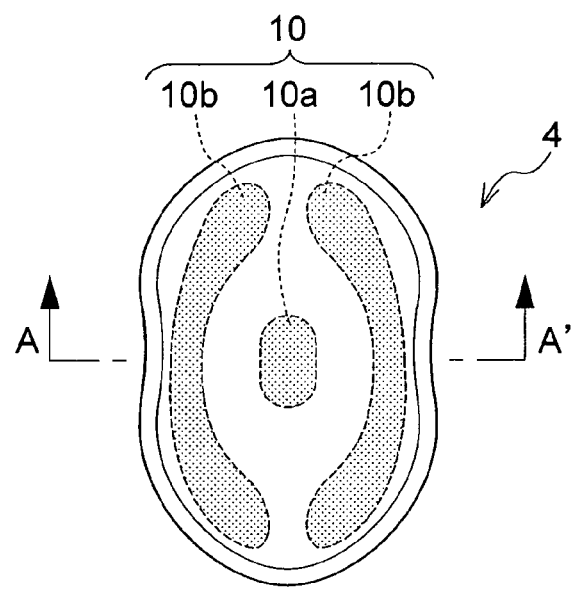
FIG. 20 is a diagram which shows a highly-compressed rigid region of an interlabial pad according to a modification 2 of the first embodiment as viewed from the face which is to be in contact with the wearer's skin.
Figure 21:
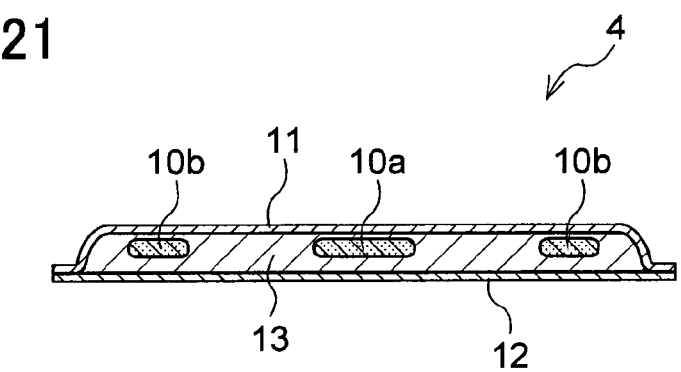
FIG. 21 is a cross-sectional view as viewed from line A-A' in FIG. 20.

An interlabial pad 4 shown in FIG. 20 has a structure in which the highly-compressed rigid region 10 is provided not only to the central region but also to the perimeters extending along the longitudinal direction. That is to say, the highly-compressed rigid region 10 is formed of a central region 10a and perimeter regions 10b. Specifically, the highly-compressed rigid region 10 is provided to three locations approximately along the lateral axis passing through the center of the interlabial pad 4. The modification 1 has generally the same structure as that of the above-described modification 1 having the approximately H-shaped pulp structure, except that pulp is eliminated from a part of the region that extends in the perpendicular direction when it is being worn.

Figure 22:
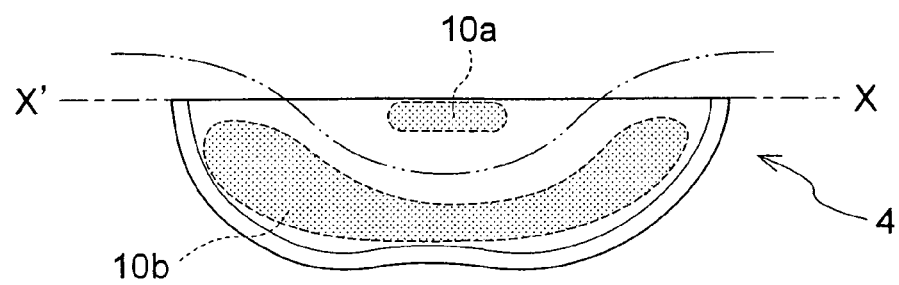
FIG. 22 is a diagram which shows the folded interlabial pad according to the modification 2 as viewed from the side.
Figure 23:
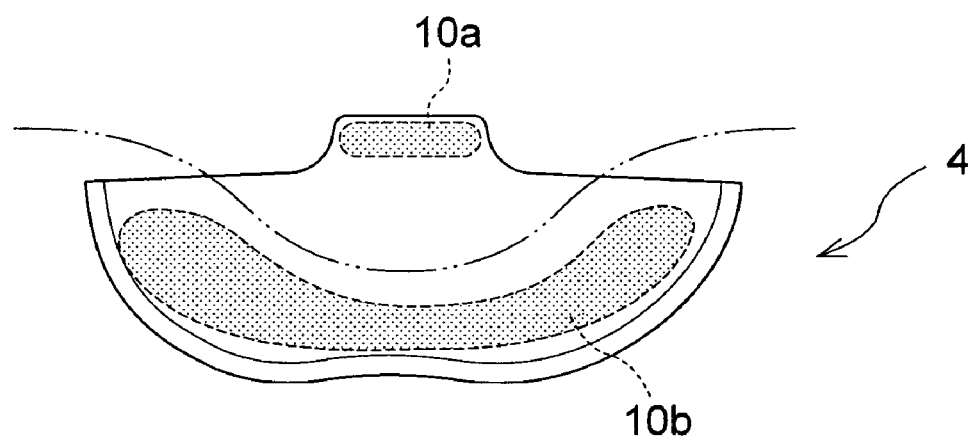
FIG. 23 is a diagram which shows the interlabial pad according to the modification 2, changing its shape when it is worn.
Figure 24:
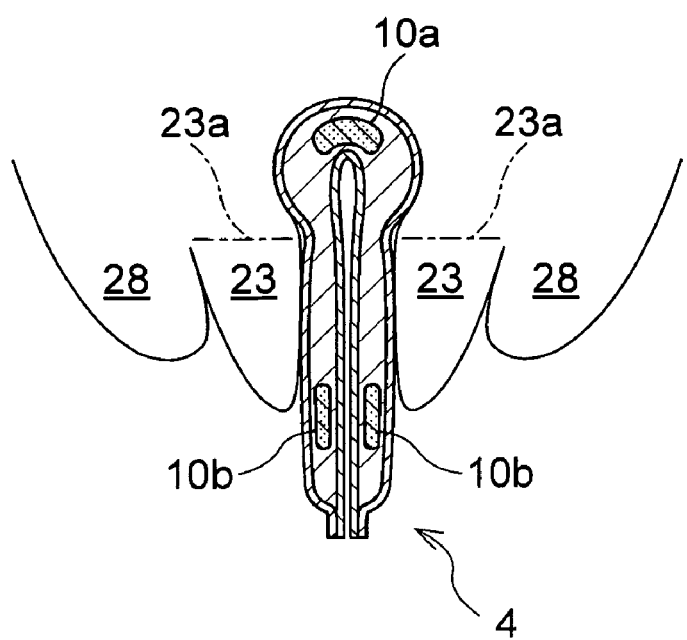
FIG. 24 is a sectional view which shows the interlabial pad according to the modification 2 when it is being worn.

As shown in FIG. 22, upon folding the interlabial pad 4 according to the Modification 2 with the center line as a reference, the highly-compressed rigid region 10 becomes a structure in which two regions extend approximately in parallel with each other along the longitudinal direction. As shown in FIG. 3, upon the interlabial pad 4 being inserted, the distance between the central region 10a and the perimeter region 10b becomes greater along the vertical direction. Accordingly, as shown in FIG. 24, the central region 10a completely fir near the vestibule, and the interlabial pad 4 is held by the base of the labia minora 23a. Such an arrangement effectively prevents displacement of the interlabial pad 4.

Modification 3

Figure 25:
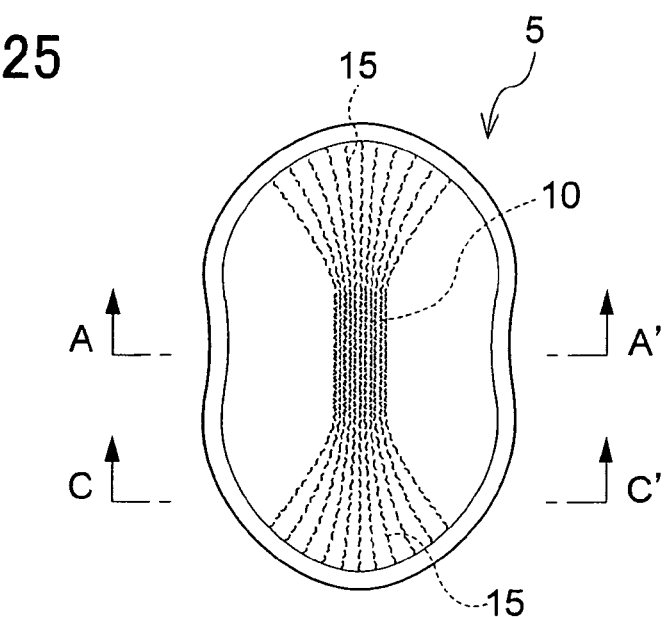
FIG. 25 is a diagram which shows a highly-compressed rigid region of an interlabial pad according to a modification 3 of the first embodiment as viewed from the face which is to be in contact with the wearer's skin.
Figure 26:
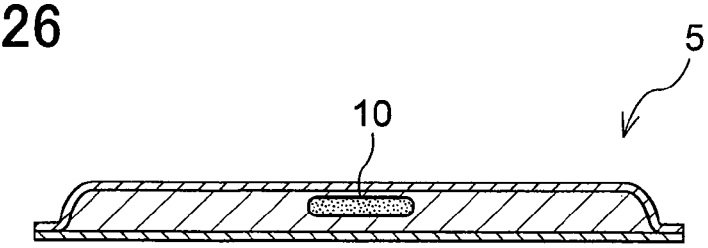
FIG. 26 is a cross-sectional view as viewed from line A-A' in FIG. 25.
Figure 27:
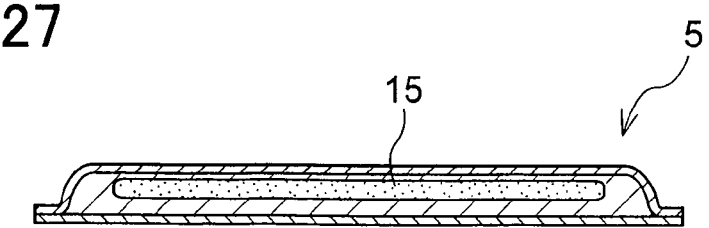
FIG. 27 is a cross-sectional view as viewed from line C-C' in FIG. 25.
Figure 28:
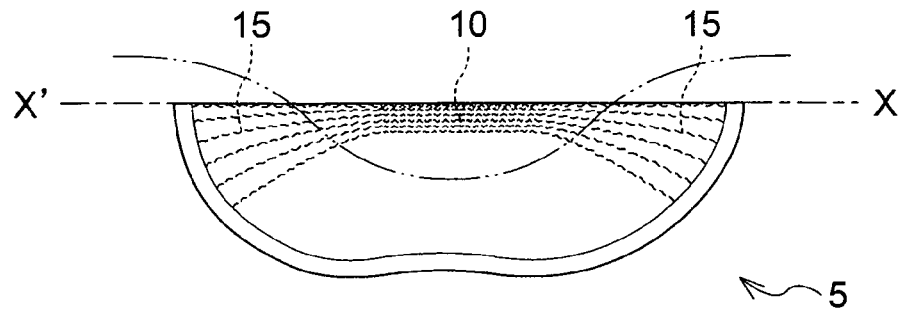
FIG. 28 is a diagram which shows the folded interlabial pad according to the modification 3 as viewed from the side.
Figure 29:
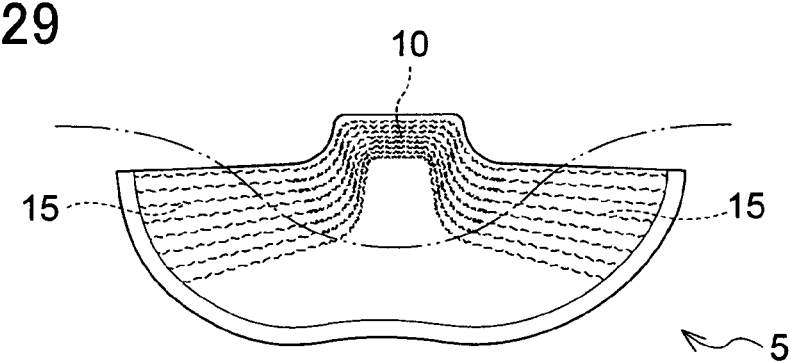
FIG. 29 is a diagram which shows the interlabial pad according to the modification 3 changing in shape when it is being inserted.
Figure 30:
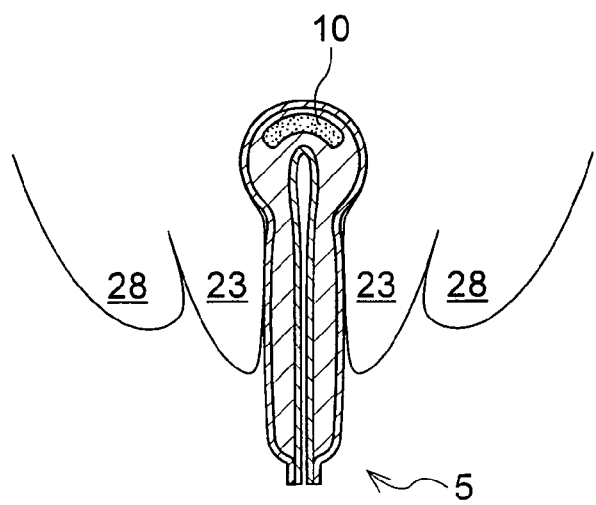
FIG. 30 is a sectional view which shows the interlabial pad according to the modification 3 when it is worn.

An interlabial pad 5 shown in FIG. 25 has a structure in which fiber assembly formed of fiber bundles, which form the absorber, is provided along the longitudinal direction. With such an arrangement, furthermore, the fiber assembly is provided with higher density around the center along the longitudinal direction, thereby forming the highly-compressed rigid region 10. That is to say, the interlabial pad 5 has a simple structure in which the fiber bundle is provided with a density adjusted corresponding to the position along the longitudinal direction. With such an arrangement, the interlabial pad 5 has the highly-compressed rigid region 10 where the fiber bundle is provided with high density along the longitudinal direction, and the other regions 15 where the fiber bundle is provided with low density with the aforementioned highly-compressed rigid region 10 being introduced therebetween. Specifically, with such an arrangement, the highly-compressed rigid region 10 is provided in a manner as shown in the cross-sectional view taken along line A-A' in FIG. 26. On the other hand, the region 15 where the fiber assembly has been provided with low density is provided in a wider area than that of the highly-compressed rigid region 10 as shown in the cross-sectional view taken along line C-C' in FIG. 27. With such an arrangement, upon folding the interlabial pad 5 along the center line X-X' extending in the longitudinal direction as shown in FIG. 28, the highly-compressed rigid region 10 is provided between the low-density fiber bundle regions. Upon the interlabial pad 5 being inserted, the highly-compressed rigid region 10 protrudes from surroundings thereof as shown in FIG. 29. With such an arrangement, as shown in FIG. 30, only the highly-compressed rigid region 10 is provided around the center when the interlabial pad 5 is being worn.

Modification 4

Figure 31:
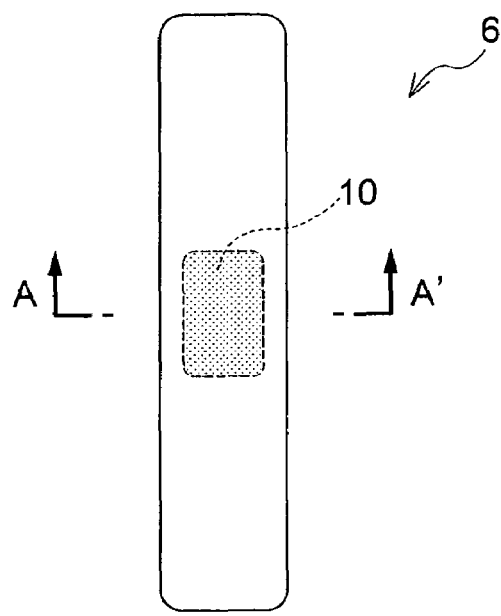
FIG. 31 is a diagram which shows an interlabial pad according to a modification 4 of the first embodiment as viewed from the face which is to be in contact with the wearer's skin.
Figure 32:
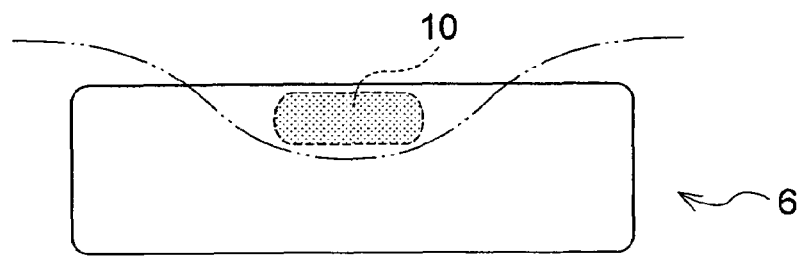
FIG. 32 is a diagram which shows the interlabial pad according to the modification 4 as viewed from the side.
Figure 33:
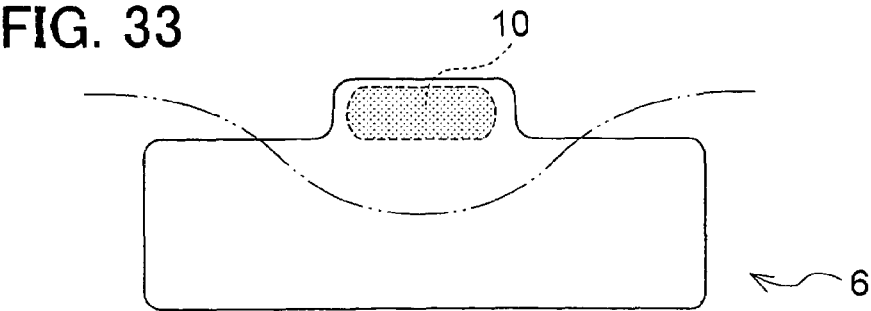
FIG. 33 is a diagram which shows the interlabial pad according to the modification 4 changing in shape when it is being inserted
Figure 34:
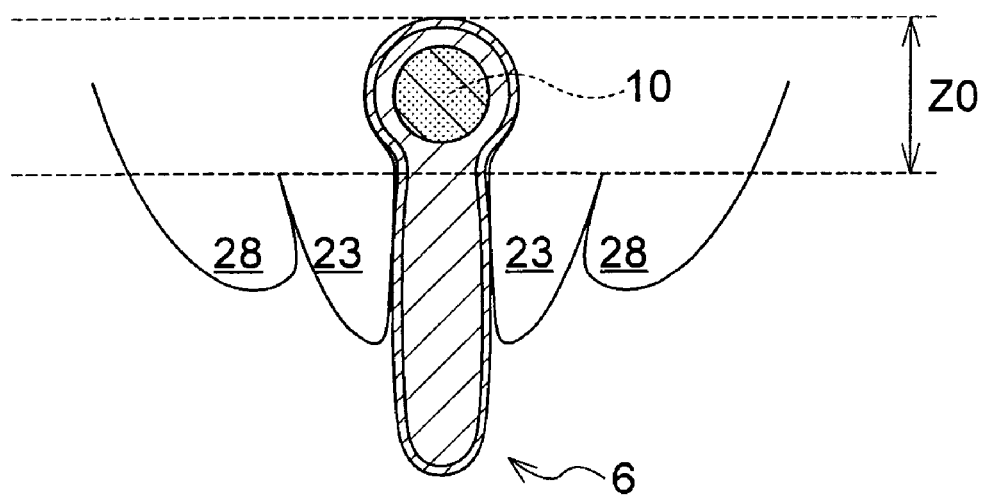
FIG. 34 is a diagram which shows the interlabial pad according to the modification 4 when it is worn.

An interlabial pad 6 shown in FIG. 31 is formed in a rectangular shape that conforms to the wearer's pudendal cleavage, which allows the wearer to wear it without the need to fold it into two. Specifically, there is no need to fold the interlabial pad 6 before the wearer wears it. Upon the interlabial pad 6 being put between the labia, the highly-compressed rigid region 10 protrudes from surroundings thereof as shown in FIG. 33. As a result, the interlabial pad 6 is inserted along the vertical direction with the highly-compressed rigid region 10 being provided at a region Z0 near the vestibule between the wearer's labia minora.

Second Embodiment

Figure 35:
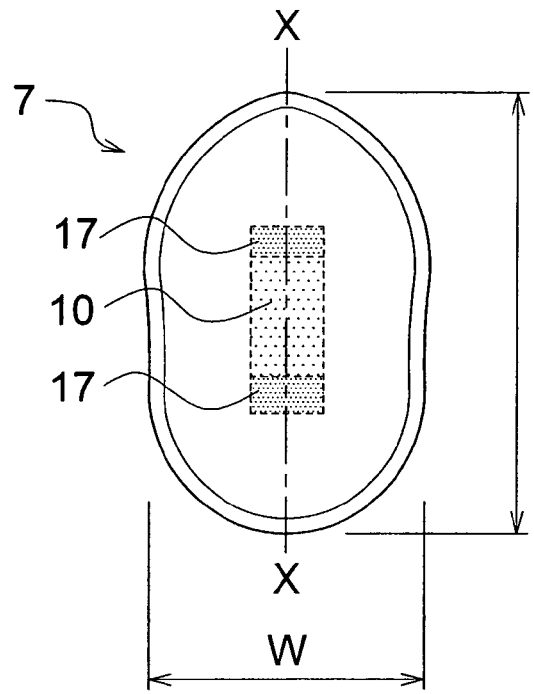
FIG. 35 is a diagram which shows an interlabial pad according to a second embodiment as viewed from the face which is to be in contact with the wearer's skin.
Figure 36:
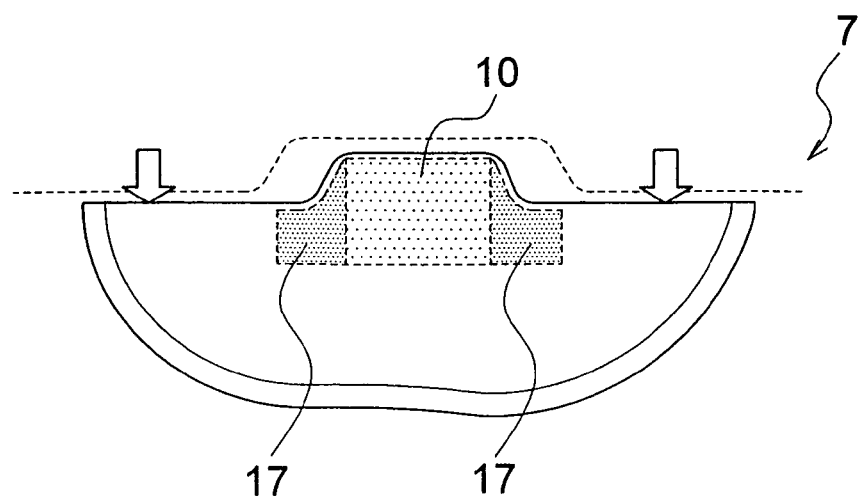
FIG. 36 is a diagram which shows the interlabial pad according to the second embodiment as viewed from the side when it is worn.
Figure 37:
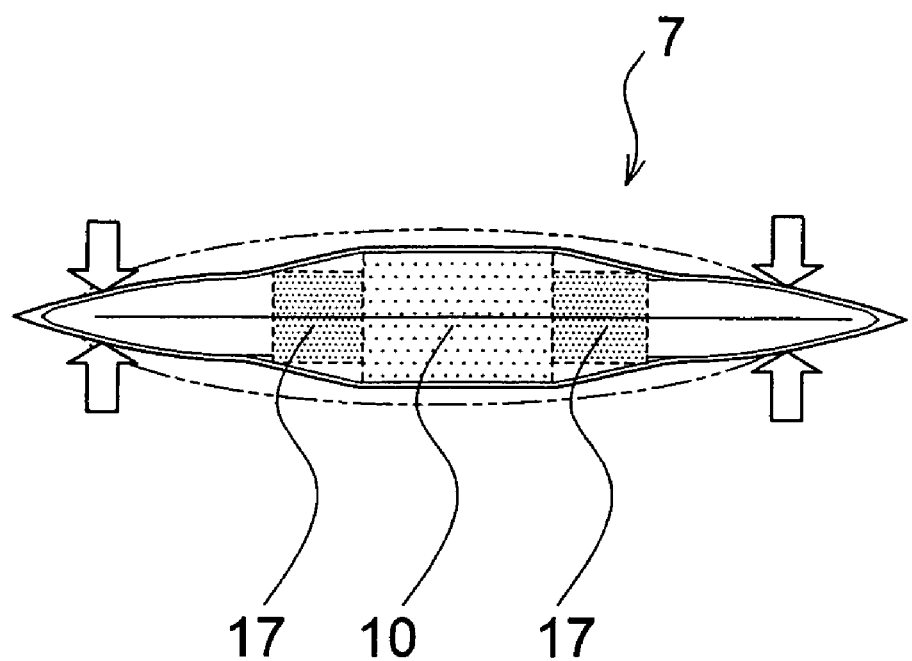
FIG. 37 is a diagram which shows the interlabial pad according to the second embodiment as viewed from the top when it is worn.

Next, a description will be given regarding an interlabial pad according to a second embodiment having a structure in which transition regions are provided to both ends of the highly-compressed rigid region along the longitudinal direction. FIGS. 35 through 37 are explanatory diagrams for describing the interlabial pad according the second embodiment when it is being worn.

As shown in FIG. 35, an interlabial pad 7 includes the highly-compressed rigid region 10, and transition regions 17, each of which smoothly connects the highly-compressed rigid region 10 and the other region, provided along the center line X-X'. Each of the transition regions 17 has a lower stiffness and lower resistance to being compressed than that of the highly-compressed rigid region 10. Furthermore, each of the transition regions 17 has a higher stiffness and higher resistance to being compressed than that of the peripheral region other than the highly-compressed rigid region 10. With such an arrangement, the stiffness and the resistance to being compressed change in a stepped manner from those of the highly-compressed rigid region 10 to those of the other region. Specifically, pulverized pulp is provided to the region adjacent to each end of the highly-compressed rigid region 10 with a pulp density smaller than that of the highly-compressed rigid region 10 by around 100 g/m$^2$. As a result, each of the transition regions 17 has stiffness and a resistance to being compressed intermediate to that of the high-compression stiffness region 10 and that of the peripheral region. Accordingly, the transition regions 17 provided to each of both ends of the highly-compressed rigid region 10 along the longitudinal direction have thicknesses smaller than that of the highly-compressed rigid region 10, and greater than that of the peripheral region other than the highly-compressed rigid region. Accordingly, with such an arrangement, when it is being inserted, the thickness in the height direction changes in a stepped manner from that of the highly-compressed rigid region 10 to that of the peripheral region through that of the transition region 17 as shown in FIG. 36. Furthermore, the thickness in the width direction also changes in a stepped manner as shown in FIG. 37. This allows the interlabial pad 7 to more easily conform to the curved shape of the labia minora when it is being worn. Such an arrangement further prevents menstrual blood from leaking from the gap between the wearer's body and the interlabial pad while providing greater comfort when it is being worn.

Third Embodiment

Figure 38:
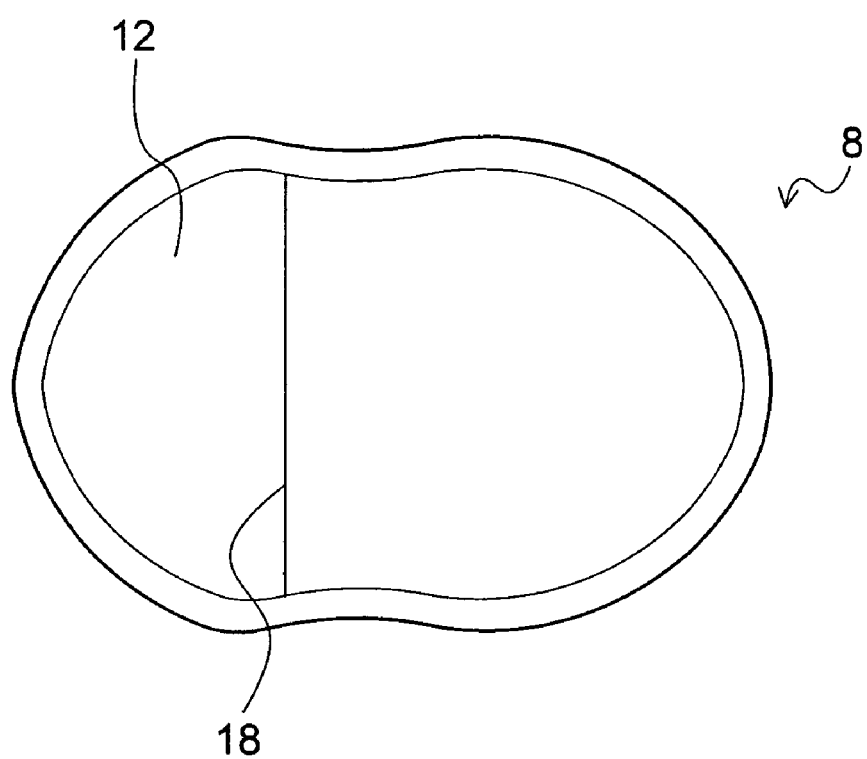
FIG. 38 is a diagram which shows an interlabial pad according to a third embodiment as viewed from the face opposite to the face which is to be inserted into the wearer's body.
Figure 39:
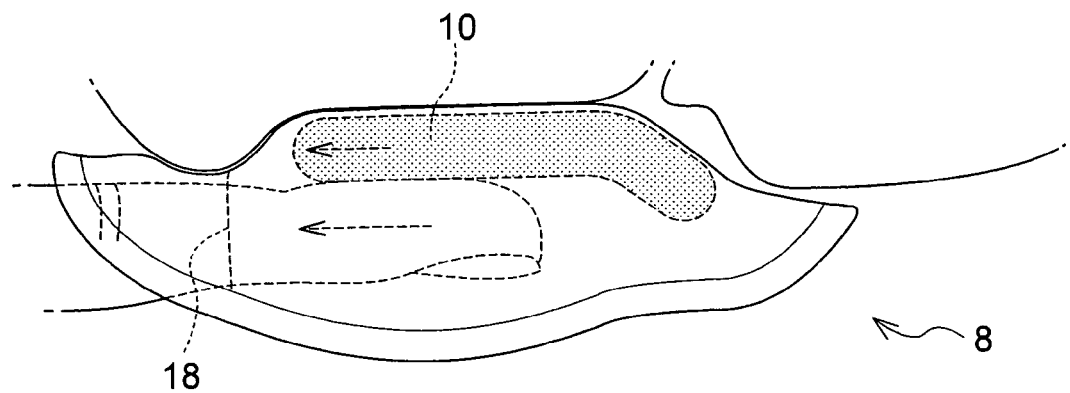
FIG. 39 is a diagram for describing the interlabial pad according to the third embodiment when it is worn.
Figure 40:
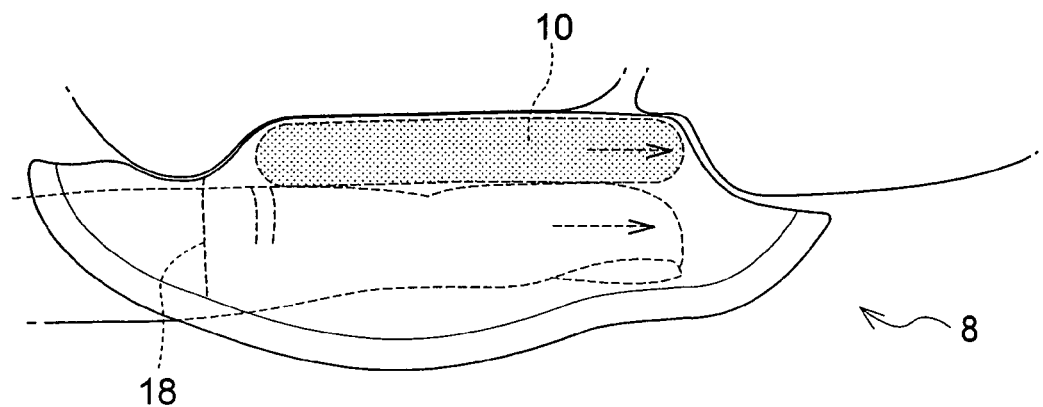
FIG. 40 is a diagram for describing the interlabial pad according to the third embodiment when it is worn.

Next, a description will be given regarding an interlabial pad the back face of which includes a pocket for allowing the insertion of the wearer's finger. FIG. 38 is a diagram which shows an interlabial pad including a finger insertion pocket having a finger insertion opening formed on the backing sheet. FIGS. 39 and 40 are diagrams which show the interlabial pad when it is being worn.

As shown in FIG. 38, an interlabial pad 8 according to the present embodiment includes a finger insertion pocket 18. Such an arrangement allows the wearer to position the wearer's sensitive finger cushion on the high-compression stiff portion 10 as shown in FIGS. 39 and 40. This allows the wearer to form a protrusion while guiding the highly-compressed rigid region 10 to a proper position between the labia minora. This allows the wearer to wear the interlabial pad 8 at a proper position in a more assured manner.

Fourth Embodiment

Figure 41:
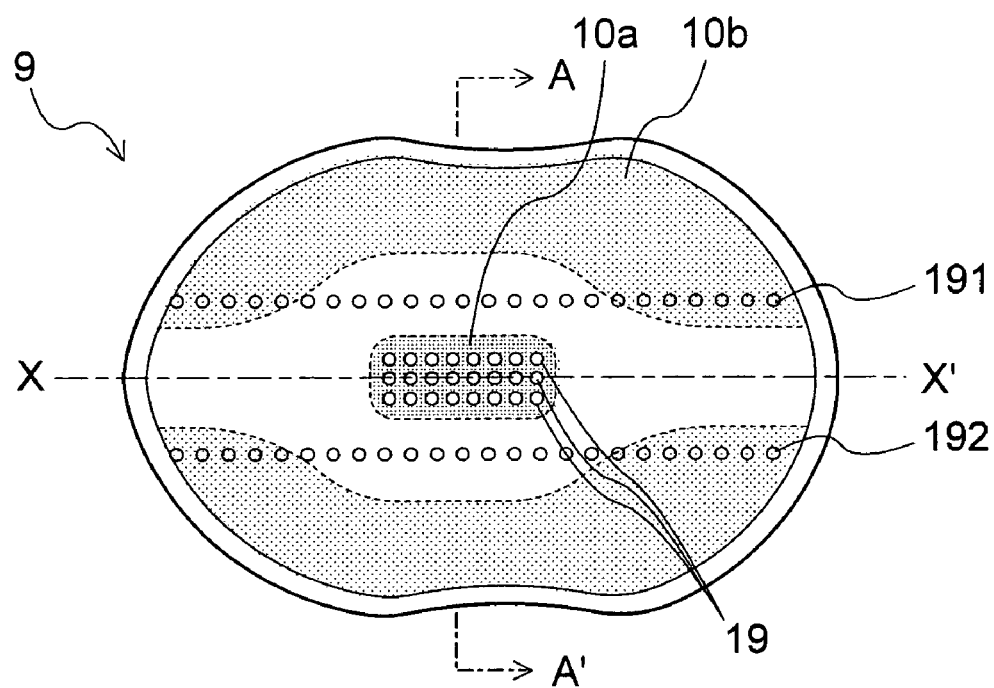
FIG. 41 is a diagram which shows an interlabial pad according to a fourth embodiment as viewed from the face which is to be contact with the wearer's skin.
Figure 42:
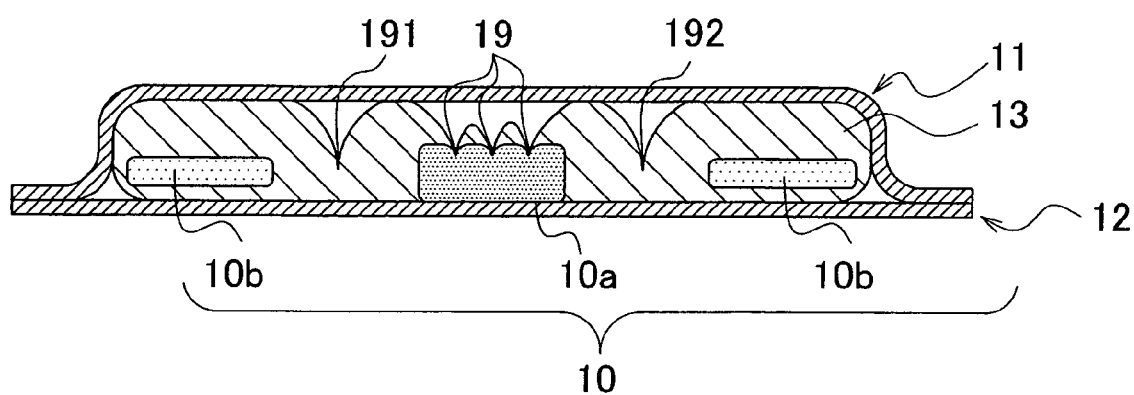
FIG. 42 is a cross-sectional view taken along line A-A' in FIG. 41.
Figure 43:
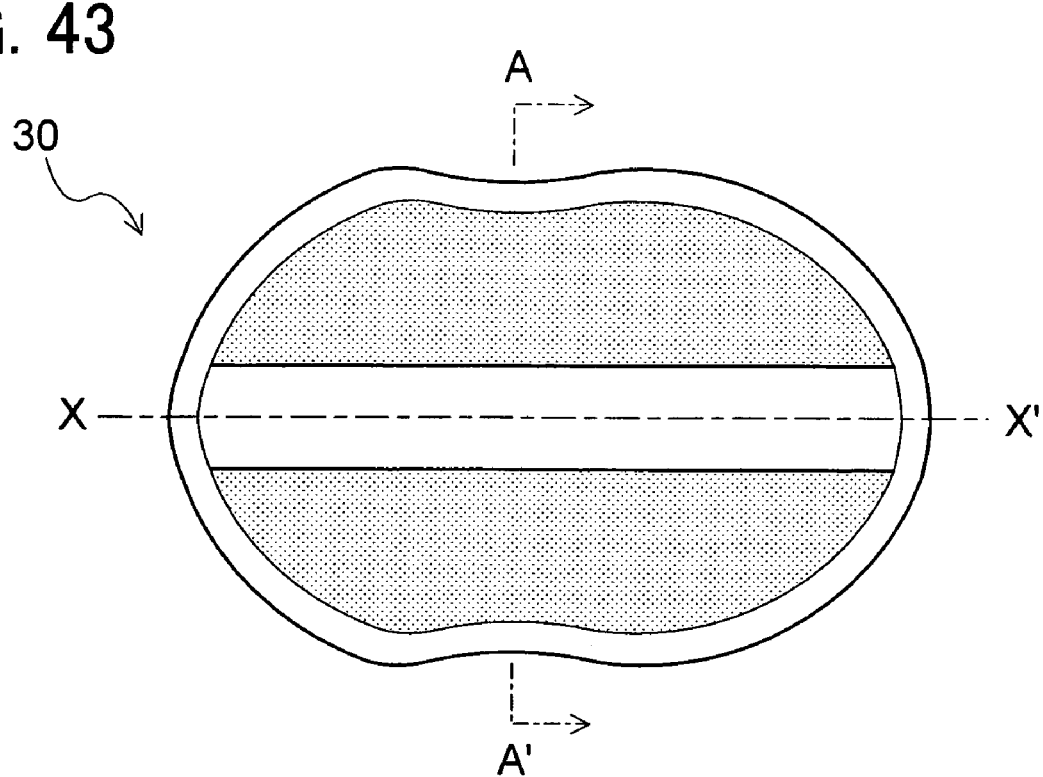
FIG. 43 is a diagram which shows an Example 1 of an interlabial pad having a function of providing a difference in thickness between the region which is inserted into the recess near the vestibule between the labia minora and the other regions of the pad.
Figure 44:
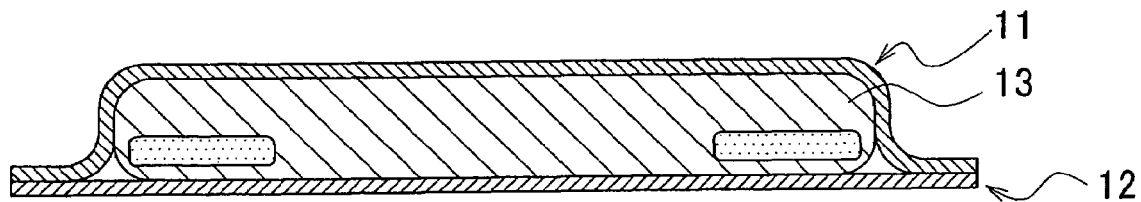
FIG. 44 is a cross-sectional view taken along line A-A' in FIG. 31.
Figure 45:
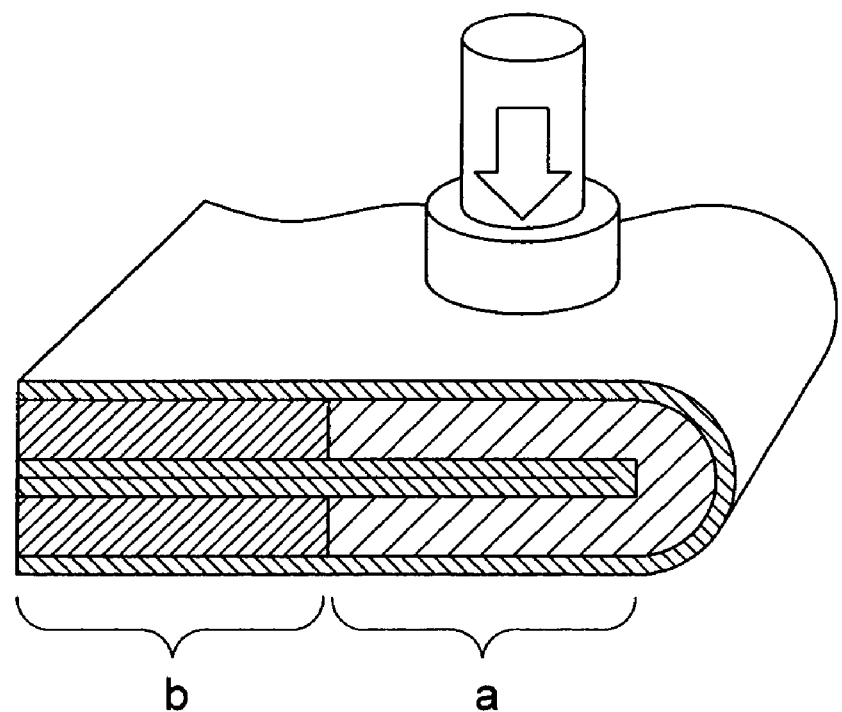
FIG. 45 is a diagram for describing a method for measuring the difference in thickness between the interlabial pad according to the fourth embodiment and the Example 1.
Figure 47:
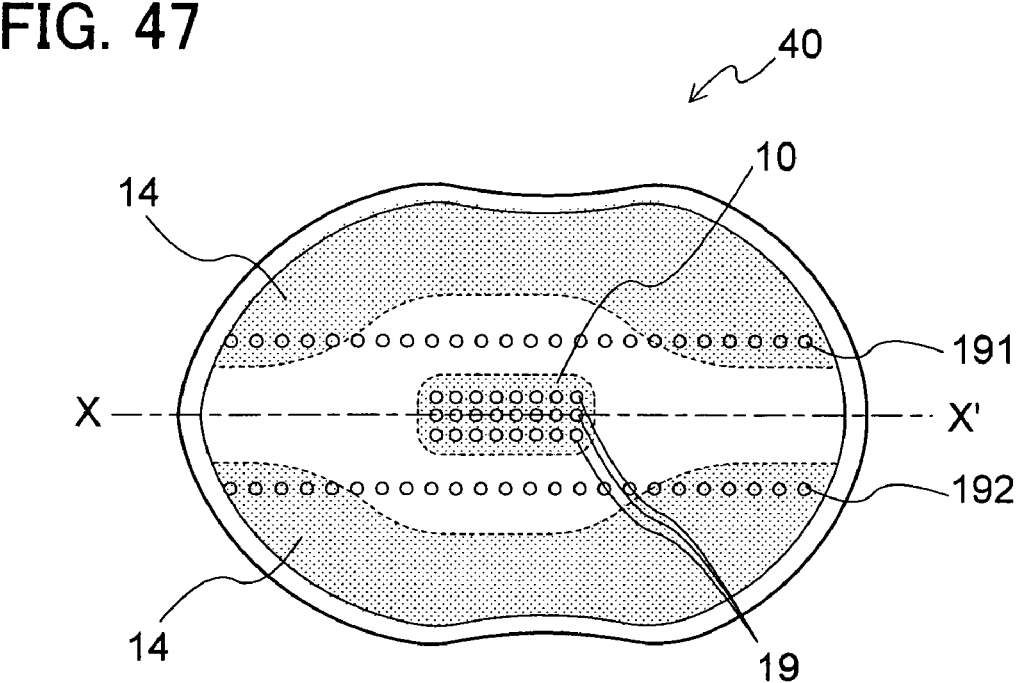
FIG. 47 is a diagram which shows an Example 2 of the interlabial pad having a function of providing a difference in thickness between the region which is inserted into the recess near the vestibule between the labia minora and the other region of the pad.
Figure 48:
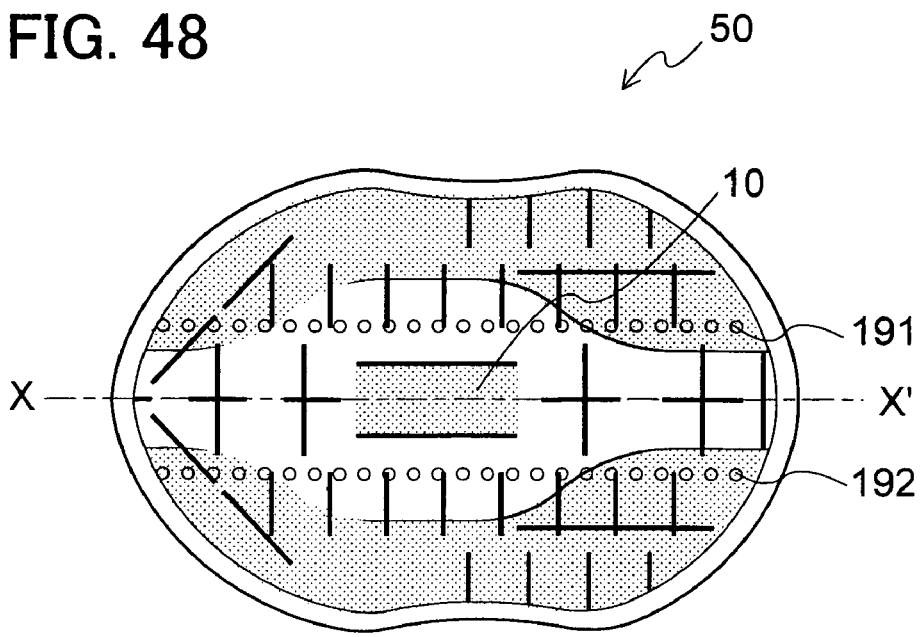
FIG. 48 is a diagram which shows an Example 3 of the interlabial pad having a function of providing a difference in thickness between the region which is inserted into the recess near the vestibule between the labia minora, and the other region of the pad.

Next, a description will be given regarding an interlabial pad having an embossed region around the highly-compressed rigid region. FIGS. 41 and 42 are diagrams which show an interlabial pad according to a fourth embodiment. FIGS. 43 through 45 are diagrams for comparison. FIGS. 47 and 48 shows other examples of interlabial pads each of which has a function of allowing the wearer to effect a difference in height between the highly-compressed rigid region and other regions.

As shown in FIG. 41, an interlabial pad 9 includes the highly-compressed rigid region 10 at the central portion of the absorber along the longitudinal direction. Furthermore, embossed regions 191, and 192 are provided in a left-right symmetrical manner with respect to the center line extending along the longitudinal direction. Such embossed regions allow the wearer to form a protrusion. As shown in the cross-sectional view in FIG. 42, the embossed regions 19, 191, and 192 are provided around the center along the longitudinal direction.

With the present invention, the portion of the interlabial pad corresponding to the recess between the labia minora is the highly-compressed rigid region 10. Accordingly, such a portion has resistance to being reduced in thickness due to being fitted to the recess between the labia minora. As described above, such an arrangement maintains the thickness of the portion which is fitted to the recess between the labia minora. This provides a difference in thickness between the highly-compressed rigid region 10 and the other region.

Figure 46:
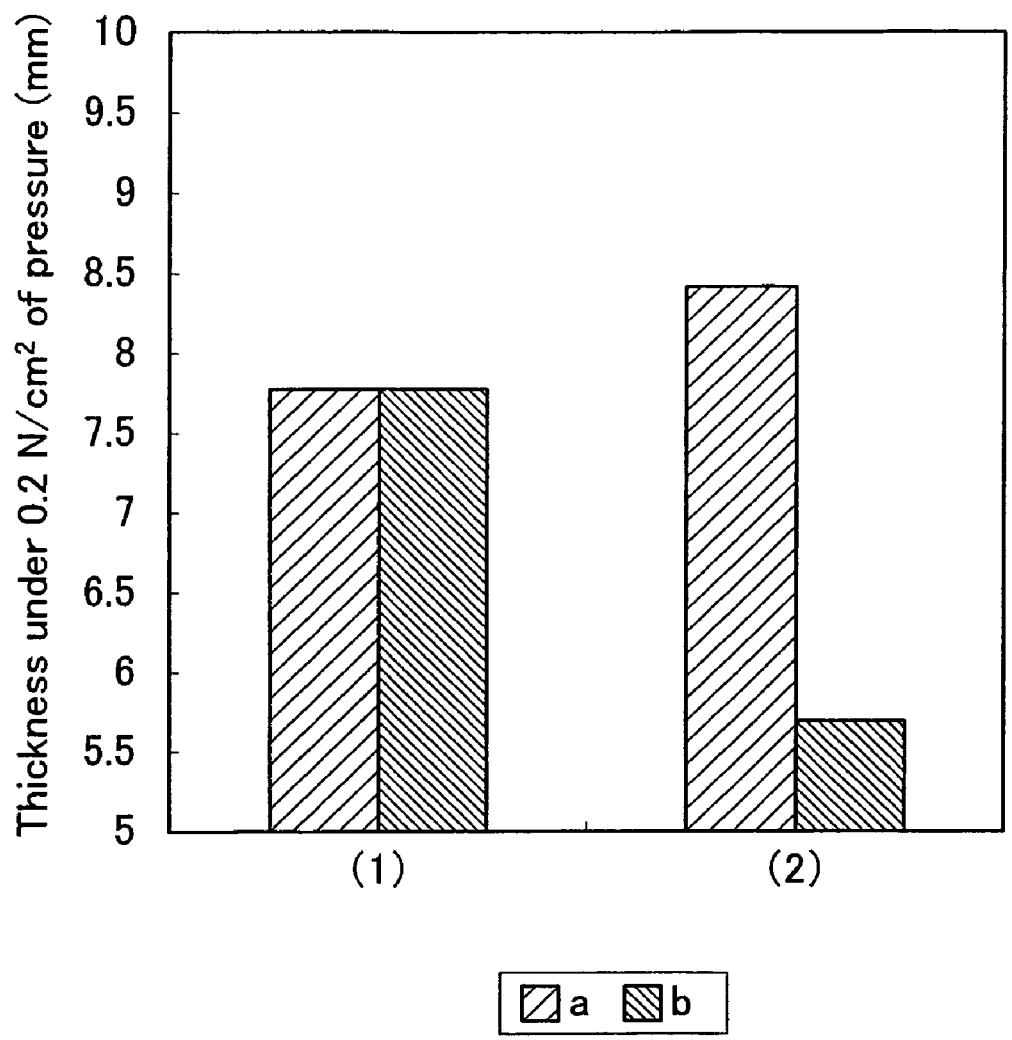
FIG. 46 is a bar graph which shows the measurement results obtained by the measurement shown in FIG. 45.

Next, a description will be given regarding the comparison between an arrangement including the highly-compressed rigid region 10 and the embossed regions as described above and an arrangement that does not have such components. FIG. 43 shows an interlabial pad 30, which is a comparison example having a structure in which pulp, which suppresses irritation applied to the clitoris and the posterior commissure of the labia when it is being worn, is not provided to the region extending along the longitudinal line. That is to say, the interlabial pad 30 has no highly-compressed rigid region around the center as shown in FIG. 44, unlike the above-described embodiment. Measurement was performed for each of the interlabial pads 30 and 9 for a difference in height between the protrusion and the surroundings thereof occurring when it is inserted. Specifically, the measurement was performed as follows. First, each of these interlabial pads is compressed along the arrow direction by a compression terminal as shown in FIG. 45. Then, the thickness of each interlabial pad was measured under 0.2 N/cm$^2$ pressure. The measurement result, as shown in graph (1) in FIG. 46, is that the interlabial pad 30 provides no difference in height. On the other hand, as shown in graph (2), the interlabial pad 9 provides a great difference in height.

As described above, an arrangement may be made, like an interlabial pad 40 shown in FIG. 47, in which the central region is formed with a high density by embossing alone, without providing any difference in pulp density between the central region and the surroundings thereof, thereby forming the highly-compressed rigid region 10. Also, an arrangement may be made, like an interlabial pad 50 shown in FIG. 48, in which the absorber outside of the highly-compressed rigid region 10 has been subjected to slit processing. Upon the insertion of such an arrangement, this provides a difference in thickness between the highly-compressed rigid region 10 and the other regions. FIG. 48 shows an arrangement in which no slit is provided along the center line in the high-compression region 10. Also, an arrangement may be made in which a slit is provided in such a region. Such an arrangement allows the wearer to fold the interlabial pad 50 into two along the slit thus provided.

Materials of Components

Front Sheet

The front sheet 11 preferably has sufficient tensile capability along the center line extending in the longitudinal direction. Such an arrangement prevents deformation of the interlabial pad in an irregular manner due to a poor tensile capability of the front sheet 11 when the highly-compressed rigid region protrudes such that it is being inserted into the recess between the labia minora. Note that the entire region of the front sheet 11 may have such sufficient tensile capability. Also, a part of the front sheet 11 may have such sufficient tensile capability.

In order to provide such tensile capability along the center line, the front sheet 11 may be notched discontinuously. However, in some cases, such an arrangement leads to a problem of the absorber 13 escaping therefrom, or leads to a problem of damaging the inner walls of the labia. Accordingly, the front sheet 11 preferably has the following structure that provides the tensile capability along the center line.

Examples of raw materials that form the front sheet 11 include: single-type synthetic fibers, and composite synthetic fibers such as a core/sheath fiber, a deflected-core core/sheath fiber, and a side-by-side type synthetic fiber, which are formed of thermoplastic resin such as polyethylene, polypropylene, polyethylene terephthalate, etc; and hydrophilic cellulose fibers such as pulp, chemical pulp, rayon, acetate, natural cotton, etc. Furthermore, a single-type or composite non-woven fabric is formed of the fiber thus prepared, by the water flow entangling method, the spunbonding method, the point-bond method, the through-air method, or the like, thereby obtaining the material of the front sheet 11. Specific examples of the materials preferably employed for the front sheet 11 include: spunlace non-woven fabric formed of a mixed fiber formed of 50 to 95% rayon or acetate and 5 to 50% polyethylene terephthalate, with a density adjusted to within a range of 20 to 60 $g/m^2$; and a tensile spunbonded non-woven fabric.

Furthermore, the front sheet 11 is preferably tensile such that, in a case in which the front sheet 11 is extended at a low speed of 100 m/minute with an interval of 100 mm between both ends to which tensile force is applied, a 5% extension of the front sheet 11 along the longitudinal direction causes a stress of 0.01 to 0.5 N/25 mm. In a case in which a 5% extension of the front sheet 11 along the longitudinal direction causes a stress smaller than 0.01 N/25 mm, it is difficult for the sheet to maintain the shape. On the other hand, in a case that the front sheet 11 is tensile such that a 5% extension of the front sheet 11 along the longitudinal direction causes a stress greater than 0.5 N/25 mm, the front sheet 11 is excessively stiffness, leading to a problem of preventing the highly-compressed rigid region from protruding from the surroundings thereof.

Let us consider a case in which the front sheet 11 is formed by the water flow entangling method. In this case, the fibers can be bonded loosely to one another by reducing the water pressure of the water flow which is applied so as to 4 entangle the fibers. Specifically, the front sheet 11 is preferably formed with a water pressure of 9 $mN/cm^2$ or less. Furthermore, let us consider a case in which the fibers contain synthetic fibers. In this case, the front sheet 11 is preferably dried at a lower temperature than the softening temperature of the synthetic fiber.

As described above, the front sheet 11 may be formed with sufficient tensile capability in a step of forming the front sheet 11. Also, additional relaxation processing may be performed for the sheet having poor tensile capability (which causes the stress higher than 0.5 N/25 mm) such that the bond between fibers relaxes, thereby increasing the tensile capability.

Examples of the relaxation methods for relaxing the bond between the fibers of the fiber assembly that forms the front sheet 11 after the formation of the front sheet 11 include tendering and embossing in an undulating manner. Such methods relax the stiffness of the sheet thus formed. Such processing may be performed for the entire area of or a part of the sheet. Note that, in order to maintain adherence between the inner walls of the labia and the front sheet 11, there is a need to maintain the flatness of the front sheet 11. Accordingly, such additional processing is preferably performed for a part of the front sheet 11.

Also, instead of the aforementioned arrangement in which the bond between the fibers that form the front sheet 11 is relaxed, an arrangement may be made in which the front sheet 11 is pleated or corrugated along a direction orthogonal to the center line extending in the longitudinal direction of the front sheet 11, thereby enabling the front sheet 11 to be extended along the center line direction. With such an arrangement, the front sheet 11 is preferably pleated with a pleat width of 1 mm or more. In a case in which the front sheet 11 is pleated with a pleat width smaller than 1 mm, the front sheet 11 cannot sufficiently follow the extension of the interlabial pad when it is folded along the center line. On the other hand, as an example of corrugating processing, the front sheet 11 is preferably corrugated with an interval of 0.5 to 3 mm between adjacent grooves, and with a groove depth of 0.1 to 3 mm. Also, as another example, an arrangement may be made in which a part of the sheet having poor tensile capability (which causes stress higher than 0.5 N/25 mm), other than the highly-compressed rigid region, is replaced by a material having the sufficient tensile capability that allows it to be extended along the center line. The material having sufficient tensile capability that allows it to be extended may be selected from among the materials described above.

Backing Sheet

The backing sheet is formed of a material having low water permeability. Examples of such materials include: polyethylene; polypropylene; polyethylene terephthalate; polyvinyl alcohol; polylactic acid; polybutyl succinate; non-woven fabric; paper sheet; and a laminate of one or more of these materials. Also, examples of such materials include an air-permeable film formed by drawing a film material containing inorganic filler.

Specific examples of such materials include a film containing low density polyethylene (LDPE) as a principal component with a pore ratio of 10% to 30%, with a pore diameter of 0.1 to 0.6 mm, and with a weight of 15 to 35 $g/mm^2$. Examples of non-woven fabrics include a spunbonded non-woven fabric; a through-air non-woven fabric; and a point-bond non-woven fabric; etc. Also, waterproof processing may be performed for such non-woven fabrics. Of these non-woven fabrics, an SMS non-woven fabric including a meltblown layer, which is formed of extra fine fibers positioned at a significantly fine pitch, is preferably employed. With regard to the weight for each layer, the SMS non-woven fabric is preferably formed of a first layer of 5 $g/mm^2$ to 15 $g/m^2$, a second layer of 1 $g/mm^2$ to 10 $g/m^2$, and a third layer of 5 $g/mm^2$ to 15 $g/m^2$.

Material of Absorber

Examples of the materials of the absorber 13 included in the interlabial pad according to the present invention include: pulp; chemical pulp; rayon; acetate; natural cotton; polymer macromolecule absorber; fibrous polymer macromolecule absorber; synthetic fiber; a foam material; etc. Such materials may be employed singly or in a mixed form. Note that such materials preferably have a sufficient bulk size, stiffness that prevents the absorber 13 from losing its shape, and chemical properties that cause little or no chemical irritation. The reason why such materials preferably have a sufficient bulk size is to provide sufficient flexibility that suppresses the wearer's feelings of discomfort. Examples of the principal components include: physically embossed rayon or acetate; and crimped chemical pulp cross-linked using a cross linking agent; composite synthetic fibers such as a core/sheath fiber, a deflected-core core/sheath fiber, and a side-by-side type synthetic fiber, which are formed of resin such as polyethylene (PE), polypropylene (PP), polyethylene terephthalate (PET), etc., making use of the thermal contraction properties of these materials. Also, such materials may contain a material having an improved molecular orientation effected by drawing fibers in a spinning step. Also, such materials may contain fibers having a non-circular cross-sectional shape such as a cross-sectional shape of the letter "Y", the letter "C", etc. Also, oil may be applied to or may be contained in the fibers so as to improve the slippage between fibers.

The absorber can be formed by opening such fibers and forming a layered structure. Such fibers may be layered in the form of a single-layer structure. Also, such fibers may be layered in the form of a multi-layered structure in which a lower layer is formed of fibers having higher hydrophilicity than an upper layer, thereby improving the capacity to absorb menstrual blood. Also, the absorber may be formed as follows. That is to say, first, the fibers are formed in the shape of a sheet using the air laid method, the spunlace method, the papermaking method, the meltblown method, or the like, for example. Then, the fiber sheet thus formed is subjected to needling processing such that fibers are entangled with one another, thereby obtaining the absorber. Also, the absorber may be formed by embossing the fiber sheet. Note that the embossing may be performed by passing the fiber sheet through the nip between the rolls having a dot-shaped pattern, a grid-shaped pattern, an undulating pattern, or the like.

Pocket for Insertion of the Wearer's Finger

With regard to the interlabial pad including a pocket for the insertion of the wearer's finger, a small sheet piece may be provided so as to form a space between the backing sheet and the small sheet piece in the form of a pocket. With such an arrangement, a finger insertion opening is formed between the small sheet piece and the backing sheet. This allows the wearer to wear the interlabial pad at a proper position in an assured manner. Note that the small sheet piece may be formed of the same material as that of the front sheet or the backing sheet. Also, examples of the materials of the small sheet pieces include: a layered structure of elastic fiber sheets; a film; a foam material having air cells.

Examples of elastic fibers include fibers formed of thermoplastic resin such as PE, PP, PET, etc., singly. Also, such examples of elastic fibers include composite fibers such as a core/sheath fiber, a deflected-core core/sheath fiber, and a side-by-side type synthetic fiber, formed of the aforementioned thermoplastic resin. Furthermore, the fibers thus formed are preferably subjected to secondary crimping using a mechanical method, thermal method, or the like. Giving consideration to the elastic force and the feelings of comfort when the interlabial pad is being worn, the fiber layer structure is preferably formed with a size of 0.5 to 8.8 dtex, and with a fiber length of 3 mm to 64 mm. Furthermore, the fiber-layer structure is preferably formed with a thickness of 0.2 mm to 3.0 mm, and is more preferably formed with a thickness of 0.5 mm to 1.5 mm. Examples of the raw materials employed for the aforementioned films include resin such as urethane, rubber, etc., having high elasticity, etc., in addition to elastic resin such as PE, PP, PET, etc. Such raw materials are extruded and molded singly, in a composite form, or in a multi-layered form by the T-die method or the inflation method. The foam material may be obtained by foaming elastic resin such as PE, PP, PET, etc., or foaming highly elastic resin such as urethane, rubber, etc. Also, cellulose sponge having an absorption capacity may be employed as the foam material. Note that the foam material may contain open air cells or closed air cells.

Examples of non-woven fabrics using elastic fibers will be listed below. Such a non-woven fabric may be formed by the through-air method in which fibers are layered by carding machine, and boding of the fibers is performed by melting the thermoplastic resin. The non-woven fabric thus formed exhibits excellent elasticity. Accordingly, such a non-woven fabric thus formed is preferably employed. Also, the point bond method, the spunbonding method, and spunlace method, each of which is commonly employed, may be employed. Also, examples of such non-woven fabrics include a spunbonded fabric and an SMS (spunbonded layer/meltblown layer/spunbonded layer) non-woven fabric. Here, the spunbonded fabric is formed by spinning continuous filaments, and bonding the spun continuous filaments to one another by thermal embossing. On the other hand, the SMS non-woven fabric is formed by spraying the meltblown fabric onto a spunbonded fabric. Also, examples of such non-woven fabrics include a non-woven fabric formed by the chemical bond method or the air laid method. With such a method, binder is applied onto the surface after formation of the fiber-layer structure. Note that such materials may be employed singly. Alternatively, such materials may be employed in the form of a multi-layered structure in which multiple layers are fixed by an adhesive or embossing. Also, such materials may be embossed so as to adjust their elasticity and thickness, thereby providing the non-woven fabric preferably employed.

Biodegradability and Hydrolyzability

The interlabial pad according to the present invention may be formed of a material having biodegradability and hydrolyzability. For example, the front sheet 11 may be formed of a hydrophilic material which causes no irritation to the wearer's skin. Examples of such materials can be employed non-woven fabric obtained by the meltblown method; the spunbonding method; the through-air method; the point bond method; the needle-punch method; wet spunlace method; etc. Note that examples of the raw materials more preferably employed for the fibers that form the interlabial pad include biodegradable resin such as polylactic acid, polybutylene succinate, etc., in addition to pulp, cotton, rayon, acetate, etc.

Examples of the materials of the backing sheet 12 include: biodegradable sheets formed of biodegradable macromolecule polymers such as polybutylene succinate, polylactic acid, etc., as a principal component; hydrolysable sheets formed of hydrolysable macromolecule polymers such as polyvinyl alcohol, alkyl cellulose, etc. Furthermore, a hydrophilic non-woven fabric is preferably provided to a part of the liquid-impermeable backing sheet such that it is to be positioned on the side opposite to the wearer's body. Such an arrangement has the advantage of preventing the interlabial pad from floating on the surface of the water in the toilet when it is disposed.

Specific examples of such materials include: a PVA film; a film sheet of which one face, both faces, or a part of the film sheet is subjected to waterproof processing using silicone or the like, PVA film into which silicone is mixed; and a film formed of a so-called biodegradable resin material such as starch, polylactic acid, polybutylene succinate which are hydrolysis, or the like. Furthermore, giving consideration to hydrophilicity as described above, examples of such materials preferably employed include a laminate paper sheet formed by adhering a hydrophilic non-woven fabric such as tissue paper or the like to one of these films or forming a laminate structure of these films and tissue paper. Also, hydrophilic fibers such as cellulose fibers, etc. may be subjected to waterproofing processing using a sizing agent or the like. In the waterproofing step, the degree of water-proofing can be adjusted by adjusting the mixture ratio of the sizing agent or the like. This provides a hydrolysable non-woven fabric having properties both of being waterproof, which is preferable when the interlabial pad is being worn, and hydrophilicity, which is preferable when it is disposed. Furthermore, inorganic pigment may be mixed to such materials in a mixture ratio of 0.1 to 5% as necessary such that it is colored.

A description will be given below regarding a specific example of the hydrolysable non-woven fabric thus formed. First, a predetermined quantity of fibers is mixed, the fiber length being 1 to 38 mm more preferably being 2 to 20 mm, and with a size of 0.8 to 3.3 dtex, the fibers having been selected from among rayon fiber, rayon acetate fiber, cotton fiber, pulp fiber, and synthetic fiber. Then, wet spunlace non-woven fabric is formed with a weight adjusted to within a range of 10 to 60 g/m$^2$, thereby obtaining the hydrolysable non-woven fabric. These non-woven fabric subjected to waterproofing processing are employed as the backing sheet. Note that examples of the waterproofing processing include: formation of a laminate structure including the hydrolysable non-woven fabric layer and a liquid-impermeable resin layer; adhesion of a film onto the hydrolysable non-woven fabric; waterproofing using a sizing agent; etc. In a case of adhering a film onto the non-woven fabric, the film with a weight of 10 to 40 g/m$^2$ is preferably adhered to the non-woven fabric at an adhesion ratio of 1 to 30% by embossing or using a hydrolysable adhesive agent. On the other hand, in a case of forming a laminate structure, the laminate structure is preferably formed with a thickness of 10 to 40 µm.

The absorber 13 may be formed of any material having a sufficient liquid (bodily liquid) absorption capacity. Furthermore, the absorber 13 is preferably formed of a material having a sufficient bulk size, stiffness that prevents the absorber 13 from losing its shape, and the chemical properties that cause little or no chemical irritation. Examples of the materials used for the absorber 13 include: pulp; chemical pulp; rayon; acetate; natural cotton; polymer macromolecule absorber; fibrous macromolecule polymer absorber; and synthetic fiber. Such materials may be employed singly or in a mixed form. Note that, giving consideration to the biodegradability and so forth of the polymer macromolecule absorber material, carboxymethyl cellulose fiber is preferably employed. Such materials may be employed in the form of a sheet or powder. The method of using such materials is not restricted in particular.

Examples of the materials which can be employed for a small sheet piece for forming a finger-insertion pocket include: a film formed of a biodegradable material such as polylactic acid, polybutylene succinate, or the like; a spun-bonded non-woven fabric; a meltblown non-woven fabric; a film and a non-woven fabric formed of a water-soluble material such as PVA, CMC, or the like; water-dispersible tissue paper formed of cellulose fiber or recycled cellulose fibers; and a spunlace non-woven fabric, etc., or the like as a principal component; etc.

More preferably, materials which can be employed for the small sheet piece is a spunbonded non-woven fabric or a meltblown non-woven fabric formed of a biodegradable material as a principal component. The non-woven fabric is formed in the shape of a sheet with a size of 0.1 to 3.3 dtex, and with a weight of 15 to 40 g m$^2$, processed by mechanical corrugating processing.

Note that a suitable adhesive may be selected from among multiple ones corresponding to the material of the sheet piece which adheres to the backing sheet 12 using the selected adhesive. For example, let us consider a case in which the backing sheet 12 is formed of a hydrolysable material such as polyvinyl alcohol or the like. In this case, the burden that the adhesive places on a purification tank is small as long as the adhesive is applied with a discontinuous pattern such as a dotted pattern, even if a pressure sensitive adhesive is employed, which contains in the form of a principal component synthetic rubber such as styrene-ethylene-butadiene-styrene-block copolymer (SEBS), styrene-butadiene-styrene-block copolymer (SBS), styrene-isoprene-styrene-block copolymer (SIS), etc., or a thermo-sensitive adhesive, which contains, in the form of a principal component, synthetic rubber such as EVA, etc. The reason is that the sheet materials, which have been made to adhere to each other in a single unit, break down the water, even if an adhesive is employed, such as a pressure sensitive adhesive, a thermo sensitive adhesive, or the like, which has difficulty in being broken down in the water. Accordingly, the interlabial pad having such a structure breaks up in the purification tank regardless of whether or not the adhesive breaks down.

Examples of the adhesives other than those described above include: a water sensitive adhesive having the property of easily being broken down in water; a biodegradable adhesive that does not easily change its solid state properties in water. In cases of employing such adhesives, the backing sheet 12 may be formed of either a hydrolysable material or a biodegradable material. Also, the application pattern of the adhesive is not restricted in particular. Specific examples of the water sensitive adhesives include: water-soluble polymer such as polyvinyl alcohol, carboxy-methyl-cellulose, gelatin, etc.; macromolecule polymers that swell in water such as polyvinyl acetate, sodium polyacrylate, etc. Specific examples of the biodegradable adhesive include: starch; sodium alginate; guar gum; gellan gum; etc. Also, such materials may be cross-linked so as to form an adhesive in the form of a gel. Such a gel adhesive thus formed may be employed.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An interlabial pad comprising:
    an oblong and liquid-permeable top sheet which faces toward a wearer's body side, having a center line as a folding axis in a longitudinal direction of the interlabial pad, the top sheet has a sufficient tensile capability along the center line extending in the longitudinal direction to prevent deformation of the interlabial pad;
    an oblong and liquid-impermeable backing sheet which faces away from the wearer's body side, of which the perimeter is bonded to the perimeter of said top sheet;
    an absorber provided between said top sheet and said baiting sheet; and
    a highly-compressed rigid region in said absorber is provided at a central region in said center line and in a width direction of the interlabial pad, and occupies substantially an entire upper half close to said top sheet in of the interlabial pad and has a size of 5 mm to 45 mm along the longitudinal direction of the interlabial pad, wherein, in a state that the interlabial pad is folded into two with said center line as a folding axis, said highly-compressed rigid region has a size of 1 mm to 8 mm formed from the center line in a direction towards the periphery of the interlabial pad and the highly-compressed rigid region has a greater thickness than that of other regions in said absorber and has higher resistance to being compressed than that of other regions in said absorber, thereby providing a protrusion corresponding to the thickness of said highly-compressed rigid region.

2. An interlabial pad according to claim 1, wherein said highly-compressed rigid region has a thickness in the perpendicular direction when said interlabial pad is being worn, which allows said highly-compressed rigid region to fit within a region near the vestibule between the wearer's labia minora.

3. An interlabial pad according to claim 1, further including a transition region around said highly-compressed rigid region, at least in said central region, which provides a change in stiffness in a stepped manner.

4. An interlabial pad according to claim 1, further including a finger-insertion pocket which is provided to the face opposite to the wearer's body when said interlabial pad is worn, and which allows the wearer to insert the wearer's finger into said pocket, thereby enabling said highly-compressed rigid region to be positioned at a proper location.

5. An interlabial pad according to claim 1, wherein said absorber comprises pulp and the content of pulp in regions along the center line, excluding the center region, is less than in the center region, and said highly-compressed rigid region is provided in approximately the shape of the letter "H".

6. An interlabial pad according to claim 1, wherein said highly-compressed rigid regions are provided to said central region and to regions along the perimeter extending along the longitudinal direction of said interlabial pad.

7. An interlabial pad according to claim 1, wherein said highly-compressed rigid region includes fiber assembly, and wherein said fiber assembly provided in said central region is formed with a higher density than that of the other regions.

8. An interlabial pad according to claim 1, wherein said highly-compressed rigid region is an embossed region.

9. An interlabial pad according to claim 6, wherein said highly-compressed rigid region is an embossed region, and wherein said embossed region is provided to both sides of said center line, parallel to, and in a left-fight symmetrical manner with respect to, said center line.

10. An interlabial pad according to claim 1, the highly-compressed rigid region is a portion of the absorber having pulp with a density of 200 to 600 g/m$^2$ is layered and compressed under high pressure by embossing.

11. An interlabial pad comprising:

an oblong and liquid-permeable top sheet which faces toward a wearer's body side having a center line as a folding axis in a longitudinal direction of the interlabial pad, the top sheet having a sufficient tensile capability along the center line extending in the longitudinal direction to prevent deformation of the interlabial pad;

an oblong and liquid-impermeable backing sheet which faces away from the wearer's body side, of which the perimeter is bonded to the perimeter of said top sheet;

an absorber provided between said top sheet and said backing sheet; and a highly-compressed rigid region in said absorber is provided at a central region in said center line and in a width direction of the interlabial pad, and occupies substantially an entire upper half close to said top sheet in the interlabial pad and has a size of 5 mm to 45 mm along the longitudinal direction of the interlabial pad, wherein in the case of an application of pressure of 2N/cm$^2$ to the interlabial pad, said highly-compressed rigid region maintains its thickness at a level greater than that of other regions of said absorber, to which the same pressure has been applied, within a range of 0.5 to 3 mm, and wherein in a state that the interlabial pad is folded in two with said center line as a folding axis, the highly-compressed rigid region has a size of 1 mm to 8 mm formed from the center line in a direction towards the periphery of the interlabial pad and the highly-compressed region has a greater thickness than that of other regions of the absorber and has a higher resistance against being compressed than that of other regions of the absorber, thereby providing a protrusion corresponding to the thickness of the highly-compressed rigid region.

12. An interbalial pad according to claim 11, wherein the highly-compressed rigid region is a portion of the absorber having pulp with a density of 200 to 600 g/m$^2$ is layered and compressed under high pressure by embossing.

\* \* \* \* \*

UNITED STATES PATENT AND TRADEMARK OFFICE
CERTIFICATE OF CORRECTION

PATENT NO. : 7,654,992 B2
APPLICATION NO. : 11/540006
DATED : February 2, 2010
INVENTOR(S) : Koichi Yamaki et al.

It is certified that error appears in the above-identified patent and that said Letters Patent is hereby corrected as shown below:

<u>In the Claims</u>

In column 22, line 63 bridging line 64, delete the last word "bait-ing" and substitute "backing" in its place.

In column 24, line 2, delete the word "left-fight" and substitute "left-right" in its place.

Signed and Sealed this

Thirteenth Day of July, 2010

David J. Kappos
*Director of the United States Patent and Trademark Office*